United States Patent
Negus et al.

(10) Patent No.: US 6,595,987 B1
(45) Date of Patent: *Jul. 22, 2003

(54) HEART SYNCHRONIZED PULSED LASER SYSTEM

(75) Inventors: Charles C. Negus, Taunton, MA (US); Robert I. Rudko, Holliston, MA (US); Stephen J. Linhares, Taunton, MA (US); Stephen M. Perez, Taunton, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/248,881

(22) Filed: Feb. 11, 1999

Related U.S. Application Data

(63) Continuation of application No. 08/190,950, filed on Feb. 3, 1994, now Pat. No. 6,113,587, which is a continuation-in-part of application No. 08/014,363, filed on Feb. 5, 1993, now abandoned, which is a continuation of application No. 07/928,531, filed on Aug. 13, 1992, now abandoned, which is a continuation of application No. 07/586,891, filed on Sep. 24, 1990, now abandoned.

(51) Int. Cl.$^7$ .............................................. A61B 18/18
(52) U.S. Cl. ........................... 606/14; 606/13; 606/15; 606/7; 607/6; 607/9; 607/17; 128/898
(58) Field of Search ................................. 606/7, 10–16, 606/41, 42, 27, 32; 607/5–9, 17, 18, 27–29; 623/3.1, 3.28; 600/16–18; 128/898

(56) References Cited

U.S. PATENT DOCUMENTS

| | | | |
|---|---|---|---|
| 3,520,295 A | 7/1970 | Kelly | 128/2.06 |
| 3,528,424 A | 9/1970 | Ayres | 128/303.1 |
| 3,659,613 A | 5/1972 | Bredemeier | 128/395 |

(List continued on next page.)

FOREIGN PATENT DOCUMENTS

| | | |
|---|---|---|
| DE | 28 09 007 A1 | 9/1979 |
| DE | 38 03 697 A1 | 8/1989 |
| EP | 0 044 019 A1 | 1/1982 |
| EP | 0 189 329 A2 | 7/1986 |
| RU | 20 26 640 | 9/1995 |
| SU | 17 54 128 | 8/1992 |
| WO | WO 89/06935 | 8/1989 |

OTHER PUBLICATIONS

JR Crew et al., "Transmyocardial Laser Revascularization by CO2 Lasers", Laser and Stent Therapy in Vascular Disease, International Congress II, Scottsdale, Arizona, Feb. 10–15, 1989.*

(List continued on next page.)

*Primary Examiner*—Linda C. M. Dvorak
*Assistant Examiner*—Ahmed Farah
(74) *Attorney, Agent, or Firm*—Fish & Richardson P.C.

(57) ABSTRACT

A heart-synchronized pulsed laser system includes a laser; means for sensing the contraction and expansion of a beating heart to be synchronized with the laser; means, responsive to the means for sensing, for generating a trigger pulse; means for positioning the leading edge of the trigger pulse; means for positioning the leading edge of the trigger pulse during the contraction and expansion cycle of the heartbeat; means for defining the width of the trigger pulse to occur during the heartbeat cycle; and means responsive to the trigger pulse for firing the laser to strike the beating heart at the time indicated by the trigger pulse position and for the period indicated by the width of the trigger pulse. In addition, the invention feature a handpiece for a medical laser system comprising a barrel for having a passage for transmitting a laser beam and a contacting wall on one end of said barrel including an aperture in communication with the passage, a solid face extending radially outward from the aperture to the periphery of said contacting wall, and a knurled surface on the face for preventing movement of the contacting wall with respect to the heart wall during surgery.

111 Claims, 9 Drawing Sheets

U.S. PATENT DOCUMENTS

| | | | | |
|---|---|---|---|---|
| 3,906,953 | A | | 9/1975 | Wallace et al. .......... 128/303.1 |
| 3,969,685 | A | | 7/1976 | Chenausky et al. ........ 331/94.5 |
| 4,123,149 | A | | 10/1978 | Chenausky et al. ......... 350/294 |
| 4,182,316 | A | | 1/1980 | Nilsson et al. .............. 128/665 |
| 4,211,229 | A | | 7/1980 | Wurster ................... 128/303.1 |
| 4,438,514 | A | | 3/1984 | Chenausky et al. ........... 372/64 |
| 4,443,877 | A | | 4/1984 | Chenausky et al. ........... 372/38 |
| 4,453,547 | A | * | 6/1984 | Castel et al. ................ 128/421 |
| 4,469,098 | A | * | 9/1984 | Davi ....................... 128/303.1 |
| 4,494,540 | A | | 1/1985 | Ferb ....................... 128/303.1 |
| 4,611,340 | A | | 9/1986 | Okazaki ...................... 378/95 |
| 4,641,650 | A | | 2/1987 | Mok ....................... 128/303.1 |
| 4,652,083 | A | | 3/1987 | Laakmann ............... 350/96.32 |
| 4,658,817 | A | | 4/1987 | Hardy ..................... 128/303.1 |
| 4,676,231 | A | | 6/1987 | Hisazumi et al. .............. 128/6 |
| 4,682,594 | A | | 7/1987 | Mok ....................... 128/303.1 |
| 4,688,892 | A | | 8/1987 | Laakmann ............... 350/96.32 |
| 4,688,893 | A | | 8/1987 | Laakmann ............... 350/96.32 |
| 4,693,556 | A | | 9/1987 | McCaughan, Jr. .......... 350/320 |
| 4,719,639 | A | | 1/1988 | Tulip ........................... 372/66 |
| 4,751,717 | A | | 6/1988 | Chenausky .................. 372/82 |
| 4,788,975 | A | | 12/1988 | Shturman et al. ......... 128/303.1 |
| 4,805,987 | A | | 2/1989 | Laakmann et al. ...... 350/96.32 |
| 4,809,284 | A | | 2/1989 | Chenausky ................... 333/24 |
| 4,850,351 | A | | 7/1989 | Herman et al. .......... 128/303.1 |
| 4,860,743 | A | | 8/1989 | Abela ...................... 128/303.1 |
| 4,896,037 | A | | 1/1990 | Shimura et al. ......... 250/327.2 |
| 4,908,585 | A | | 3/1990 | Chenausky .................. 333/24 |
| 4,913,142 | A | | 4/1990 | Kittrell et al. ................. 606/7 |
| 4,917,084 | A | | 4/1990 | Sinofsky ........................ 606/7 |
| 4,930,863 | A | | 6/1990 | Croitoriu et al. ........ 350/96.32 |
| 4,967,745 | A | * | 11/1990 | Hayes et al. ............. 128/303.1 |
| 4,985,028 | A | | 1/1991 | Isner et al. .................... 606/15 |
| 4,997,431 | A | | 3/1991 | Isner et al. .................... 606/15 |
| 4,998,933 | A | * | 3/1991 | Eggers et al. ................. 606/41 |
| 5,062,842 | A | | 11/1991 | Tiffany ......................... 606/3 |
| 5,125,926 | A | * | 6/1992 | Rudko et al. ................. 606/19 |
| 5,269,778 | A | * | 12/1993 | Rink et al. .................... 606/12 |
| 5,490,516 | A | * | 2/1996 | Hutson ....................... 128/696 |
| 5,766,163 | A | * | 6/1998 | Mueller et al. ................. 606/7 |
| 5,797,849 | A | * | 8/1998 | Vesely et al. ............... 600/461 |
| 5,807,388 | A | * | 9/1998 | Jeevanandam et al. ....... 606/15 |
| 6,023,638 | A | * | 2/2000 | Swanson .................... 600/510 |
| 6,032,674 | A | * | 3/2000 | Eggers et al. ............... 128/898 |
| 6,171,303 | B1 | * | 1/2001 | Ben-Haim et al. ............ 606/15 |
| 6,246,898 | B1 | * | 6/2001 | Vesely et al. ............... 600/424 |
| 6,447,504 | B1 | * | 9/2002 | Ben-Haim et al. ............ 606/15 |

OTHER PUBLICATIONS

Complaint for Declaratory Relief of Patent invalidity and Non–infringement Under 28 U.S.C. §§ 2201 and 2202, filed Sep. 10, 1996.

PLC Medical Systems, Inc.'s Answer and Counterclaim, filed Oct. 15, 1996.

PLC Medical's Motion to Dismiss for Failure to State a Claim or, in the Alternative, for More Definite Statement, filed Oct. 15, 1996.

CardioGenesis's Reply to PLC Medical Systems, Inc.'s Counterclaim, served Nov. 7, 1996.

CardioGenesis' Notice of Expedited Motions, served Nov. 18, 1996.

Initial Disclosure of Defendant PLC Medical Systems, Inc. Pursuant to Fed. R. Cir. P. 26(a)(1) and Civil L.R. 16–5, served Dec. 19, 1996.

Initial Disclosure of Plaintiff CardioGenesis, served Dec. 19, 1996.

Joint Case Management Statement and Proposed Order, filed Jan. 9, 1997.

Plaintiff CardioGenesis' First Set of Requests for Production of Documents and Things from Defendant PLC Medical Systems, Inc., served Feb. 25, 1997.

Plaintiff CardioGenesis' First Set of Interrogatories to PLC Medical Systems, Inc., served Feb. 25, 1997.

PLC Medical Systems, Inc.'s Responses to CardioGenesis' First Set of Requests for Production of Documents and Things [Nos. 1–108], served Mar. 27, 1997.

Declaration of Wayne P. Sobon in Support of PLC Medical Systems, Inc.'s Opposition to CardioGenesis' Motion for Protective Order to Prevent Discovery Abuses, filed Jun. 13, 1997.

Memorandum of Points and Authorities of San Francisco Heart Institute and John Crew, M.D. in Opposition to Plaintiff's Request for Sanctions included in Motion for Protective Order, served Jun. 13, 1997.

Declaration of Rebecca R. Paul in Opposition to Plaintiff's Request for Sanctions included in Motion for Protective Order, served Jun. 13, 1997.

Order Granting Plaintiff's Motion for Protective Order, filed Jun. 23, 1997.

CardioGenesis Reply in Support of Motion to Amend Complaint and Opposition to PLC Motion for Sanctions, served Oct. 8, 1997.

PLC Medical Systems, Inc.'s Motion for a Protective Order, filed Oct. 16, 1997.

Declaration of Wayne P. Sobon in Support of PLC Medical Systems, Inc.'s Motion for a Protective Order, filed Oct. 16, 1997.

Plaintiff CardioGenesis' Second Set of Requests for Production of Documents and Things from Defendant PLC Medical Systems, Inc., served Oct. 24, 1997.

Order Granting CardioGenesis's Motion to Amend Complaint; Denying PLC's Motion for Sanctions, filed Oct. 27, 1997.

PLC's Answer to Amended Complaint for Declaratory Relief of Patent Invalidity, Non–infringement and Unenforceability Under 28 U.S.C. §§ 2201 and 2202 Counterclaim, filed Nov. 13, 1997.

Opposition to PLC's Motion for Protective Order and Application for Monetary Sanctions, served Nov. 21, 1997.

Letter from Coe A. Bloomberg to Magistrate Judge Edward A. Infante requesting modification of ruling, dated Jan. 8, 1998.

Hearing Transcript for Plaintiff's Motion for a Protective Order to Prevent Discovery Abuses, heard Jun. 23, 1997.

CardioGenesis' Supplemental Responses to PLC's First Set of Interrogatories, served Jan. 19, 1998.

PLC's Opposition to CardioGenesis' Motion for a Bifurcation of (1) Inequitable Conduct and (2) Damages and Willfulness, filed Jan. 21, 1998.

PLC's Corrected Opposition to CardioGenesis's Motion for a Bifurcation of (1) Inequitable Conduct and (2) Damages and Willfulness, filed Jan. 22, 1998.

PLC's Motion for Leave to File a Surreply and Surreply to CardioGenesis' Motion for Bifurcation, filed Feb. 4, 1998.

PLC's Supplement to Opposition to CardioGenesis's Motion for a Bifurcation of (1) Inequitable Conduct and (2) Damages and Willfulness, filed Feb. 9, 1998.

PLC's Motion to Stay Pending Reissue Examination fo the Patent–in Suit and Memorandum in Support, filed Feb. 9, 1998.

Lexis and MPEP Authorities Cited in Support of PLC's Motion to Stay, filed Feb. 9, 1998.

Order Denying CardioGenesis' Motion to Compel Production of Privileged Documents Pursuant to the Crime–Fraud Exception, filed Feb. 12, 1998.

Order Denying CardioGenesis' Motion to Bifurcate Trial on Inequitable Conduct, Willfulness and Damages, filed Feb. 12, 1998.

CardioGenesis' Motion to Compel Production of Reissue Application, served Feb. 13, 1998.

CardioGenesis' Opposition to PLC's Motion to Stay this Litigation Pending PTO Reissue Examination of the Patent–in–Suit, served Feb. 13, 1998.

PLC's Reply to Motion for a Protective Order, filed Dec. 1, 1997.

PLC's Reply in Support of Motion to Stay Pending Reissue Examination, filed Feb. 24, 1998.

L. Junquiera, G. Bignolas, P.R. Brenttani, "Picrosirius Staining Plus Polarization Microscopy, a Specific Method for Collagen Detection In Tissue Sections," Histochem J 11 447–455 (1979).

Zaitzev, V.T., et al., "The Fiber–Laser Devices for Vascularization of The Miocard," Internat. Conf. Lasers and Medicine Part 3, Moscow, Oct. 10, 1989.

Desilets–Hoffman, United States Catheter & Instrument Corporation, 07/65.

Beck, Claude S., "The Development of a New Blood Supply to the Heart by Operation," Annals of Surgery 102:801–813, 1935.

Cottier, Christoph, et al., "Multiple Coronary Arteriocameral Fistulas as a Cause of Myocardial Ischemia," American Heart Journal 115:181–184, 01/88.

Goldman, Alfred, et al., "Experimental Methods for Producing a Collateral Circulation to the Heart Directly from the Left Ventricle," Journal of Thoracic Surgery 31:364–374, 03/56.

Hardy, Roger Ian, et al., "A Histologic Study of Laser–Induced Transmyocardial Channels," Lasers in Surgery and Medicine 6:563–573, 1987.

Hardy, R.I., et al., "Regional Myocardial Blood Flow and Cardiac Mechanics in Dog Hearts with CO2 Laser–Induced Intramyocardial Revascularization," Basic Research in Cardiology 85:179–197, 1990.

Khazei, A. Hassan, et al., "Myocardial Canalization: A New Method of Myocardial Revascularization," Annals of Thoracic Surgery 6:163–171, 08/68.

Aretz, H.T., et al., "Intraluminal Ultrasound Guidance of Transverse Laser Coronary Atherectomy," SPIE 1201:68–78, 1990.

Massimo, C., et al., "Myocardial Revascularization by a New Method of Carrying Blood Directly from the Left Ventricular Cavity into the Coronary Circulation," Journal of Thoracic Surgery 34:257–264, 8/57.

Mirhoseini, Mahmood, et al., "Clinical and Histological Evaluation of Laser Myocardial Revascularization," Journal of Clinical Laser Medicine & Surgery 73–78, 06/90.

Mirhoseini, Mahmood, et al., "Lasers in Cardiothoracic Surgery," Lasers in General Surgery 216–232, 1989.

Mirhoseini, Mahmood, et al., "New Concepts in Revascularization of the Myocardium," Annals of Thoracic Surgery 45:415–420, 04/88.

Mirhoseini, Mahmood, et al., "Revascularization of the Heart by Laser," Journal of Microsurgery 2:253–260, 06/81.

Mirhoseini, Mahmood, "Laser Applications in Thoracic and Cardiovascular Surgery," Medical Instrumentation 17:401–403, 11–12/83.

Mirhoseini, Mahmood, "Laser Revascularization of the Heart," New Frontiers in Laser Medicine and Surgery (Atsumi, Editor), ISPN Elsevier Science Publishing Co., 296–303, 1982.

Mirhoseini, Mahmood, et al., "Transventricular Revascularization by Laser," Lasers in Surgery and Medicine 2:187–198, 1982.

O'Connor, William N., et al., "Ventriculocoronary Connections in Hypoplastic Left Hearts: An Autopsy Microscopic Study," Circulation 66:1078–1086, 11/82.

Okada, Massayoshi, et al., "Laser Application in the Fields of Cardiovascular Surgery," YAG Laser in Medicine and Surgery, 319–323, 1986.

Pifarre, Roque, "Intramyocardial Pressure During Systole and Diastole," Annals of Surgery 168:871–875, 11/68.

Pifarre, Roque, et al., "Myocardial Revascularization by Transmyocardial Acupuncture," Journal of Thoracic and Cardiovascular Surgery 58:424–431, 09/69.

Renault, Guy, et al., "In Situ Monitoring of Myocardial Metabolism by Laser Fluorimetry: Relevance of a Test of Local Ischemia," Lasers in Surgery and Medicine 5:111–122, 1985.

Rissel, U., et al., "A New 2–Channel Stimulation Device with an Integrated Ablation–control Unit for the Diagnosis and Treatment of Cardiac Arrhythmia," Biomedizinische Technik 33:18–25, 1988.

Sen, P.K., et al., "Transmyocardial Acupuncture," Journal of Thoracic and Cardiovascular Surgery 50:181–189, 08/65.

Vineberg, Arthur, "Clinical and Experimental Studies in the Treatment of Coronary Artery Insufficiency by Internal Mammary Artery Implant," Journal of the International College of Surgeons 22:503–518, 1954.

Walter, P., et al., "Treatment of Acute Myocardial Infarction by Transmural Blood Supply from the Ventricular Cavity," European Surgical Research 3:130–138, 1971.

Wearn, Joseph T., et al., "The Nature of the Vascular Communications Between the Coronary Arteries and the Chambers of the Heart," The American Heart Journal 9:143–164, 1933.

CardioGenesis Corporation's Notice of Opposition Against a European Patent No. EP 0 553 576 B1 with attachments, dated Apr. 17, 1996.

Mirhoseini, Mahmood, et al., "Myocardial Revascularization by Laser: A Clinical Report," Lasers in Surgery and Medicine 3:241–245, 1983.

SCIMED Life Systems, Inc.'s Notice of Opposition Against a European Patent No. EP 0 553 576 B1 with attachments, dated Apr. 17, 1996.

J.R. Crew et al., Abstract, "Transmyocardial Laser Revascularization by $CO_2$ Laser," Laser and Stent Therapy in Vascular Disease, Int'l Congress II in Scottsdale, Arizona, Feb. 10–15, 1989.

J.R. Crew et al., Abstract, "Transmyocradial Revascularization by 750 Watt $CO_2$ Laser: Sole Therapy," Lasers, Stents and Interventions in Vascular Disease, Int'l Congress III in Scottsdale, Arizona. Feb. 11–16, 1990.

M. Mirhoseini, et al., *Clinical Report: Laser Myocardial Revascularization*, Lasers in Surgery and Medicine 6, 459–461 (1986).

Order Construing Claims; Denying CardioGenesis' Motion for Summary Judgment Regarding (1) Materiality, (2) Intent, and (3) Inequitable Conduct; Granting PLC's Countermotion for Summary Judgment of No Inequitable Conduct, Civil No. 96–20749 SW, N.D. Cal., Dec. 2, 1998.

Bloomberg, Coe, Letter to Hon. Spencer Williams, Dec. 2, 1998.

CardioGenesis L.R. 7–10 Motion for Leave to File (1) A Motion for Reconsideration of the Court's Conclusion That Counsel Misrepresented Facts and (2) A Motion for Reconsideration of the Court's Order Granting Summary Judgment of No Inequitable Conduct, Case No. C96–20749 SW (EAI), N.D. Cal., Dec. 14, 1998.

Plaintiff CardioGenesis Corp. Motion for Reconsideration Under Local Rule 7–9 of Order Granting Summary Judgment of Inequitable Conduct to PLC, Case No. C96–20749 SW (EAI), N.D. Cal., Dec. 9, 1998.

* cited by examiner

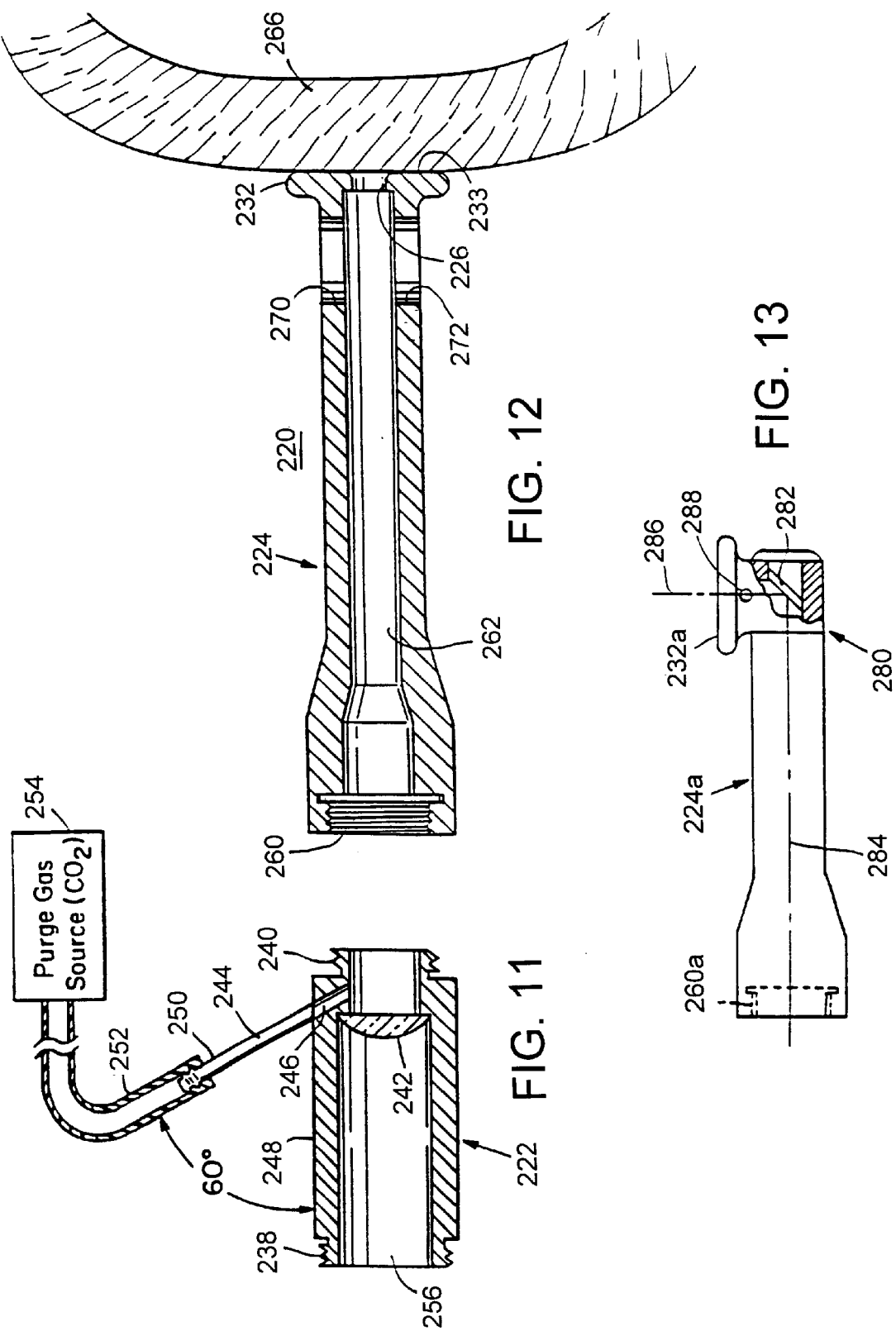

HEART SYNCHRONIZED PULSED LASER SYSTEM

CROSS REFERENCE TO RELATED APPLICATIONS

This application is a continuation of Ser. No. 08/190,950 filed Feb. 3, 1994 now U.S. Pat. No. 6,113,587 which is a continuation-in-part application of Ser. No. 08/014,363 filed Feb. 5, 1993 which is a continuation of Ser. No. 07/928,531 filed Aug. 13, 1992 which is a continuation of Ser. No. 07/586,891 filed Sep. 24, 1990. This application incorporates herein by reference the following applications having common inventors and assignee: "Heart Synchronized Vacuum-Assisted Pulsed Laser System and Method", by Robert I. Rudko; application Ser. No. 586,885 filed Sep. 24, 1990 issued as U.S. Pat. No. 5,109,388 and application Ser. No. 586,951 filed Sep. 24, 1990 issued as U.S. Pat. No. 5,125,926.

FIELD OF INVENTION

This invention relates to a heart-synchronized pulsed laser system, and more particularly to such a system which operates on a beating heart between the R and T waves of the electrocardiogram (ECG) signal, and to a handpiece for a medical laser system.

BACKGROUND OF THE INVENTION

The heart muscle receives its blood supply from the coronary artery, which feeds out and around into the outside of the heart muscle. Some time ago it was noticed that reptilian hearts had no arterial supply to the heart muscle. Rather, the reptilian heart blood supply was delivered through the inside wall of the heart directly to the heart muscle. The thought occurred that this could be an alternative to the heart bypass technique which can usually be applied to a patient no more than twice: after two bypass operations the risks outweigh the benefits and the patient is generally without further recourse. In an attempt to imitate the reptilian condition, tiny holes were made in mammalian hearts with hot wires or needles but this met with limited success. Although the holes healed from the outside and did allow for some internal blood delivery, the holes soon healed over entirely and cut off the blood supply. The protocol was then developed using a laser to make the holes and this met with much greater success. This technique is known as transmyocardial revascularization (TMR). However, the laser technique introduced a host of new problems. The heart is extremely sensitive to a laser pulse at certain times during its cycle. A laser pulse striking the heart at the T time of the ECG wave, for example, could cause the heart to fibrillate and result in heart failure. If the heart is stopped during the procedure this problem can be avoided. But stopping the heart requires cooling the heart and connecting the patient to a heart-lung machine with all the attendant increased risks that this brings including prolonged recovery times. A beating heart, on the other hand, is difficult to administer this technique to because as the heart contracts and expands the surface may not remain normal to the laser beam, the heart wall changes distance from the focus of the beam, and the thickness of the wall changes so that the positioning of the laser handpiece and the power of the beam required are varying and unpredictable. This makes precise location of laser beam on the heart difficult so that not only will the holes not be properly located, but other areas of the heart which should not be struck may well be struck. Further, when the technique requires stopping the heart the chest must be cut open including cutting the sternum, which is especially risky because the sternum is a primary source of red blood cells.

A beating heart is electrically active and the contact of a handpiece against the heart wall may disrupt that electrical activity and interfere with the heart function. Arrhythmia and fibrillation can occur and can result in heart failure. Further, any interference with the electrical field of the heart interrupts the synchronous operation of laser so that the laser is no longer constrained to fire at the optimum moment in the beating heart cycle. The current handpiece used with $CO_2$ lasers have a relatively sharp tip on a gauge rod extending from the end of the handpiece used to consistently position the handpiece at the proper distance from the stilled heart wall for accurate laser beam focusing and impingement. Such a tip creates increased pressure on the heart, which can cause arrhythmia, fibrillation, and can even puncture the wall of the heart. Further, with these handpieces it is difficult to maintain the laser beam perpendicular with the wall of a beating heart as is necessary to effect clean, correctly placed holes in the heart wall. Finally, these handpieces may slide on the heart wall during the procedure disrupting the surgeon's concentration.

SUMMARY OF THE INVENTION

It is therefore an object of this invention to provide a laser system for performing transmyocardial revascularization on a beating heart.

It is a further object of this invention to provide such a laser system which is synchronized to operate at a specific time in the heart's beating cycle when accuracy is enhanced and risks are reduced.

It is a further object of this invention to provide such a laser system which is synchronized to operate between the R and T waves of the heart's ECG.

It is a further object of this invention to provide such a laser system which provides shorter pulses that interfere less with the heart function and make cleaner holes.

It is a further object of this invention to provide such a laser system which times the laser pulses to occur when the heart surface is relatively stable to enhance the accuracy of laser aiming and focusing and minimize the risk of striking an undesirable part of the heart.

It is a further object of this invention to provide such a laser system which times the laser pulses to occur when the heart wall is at a point in its cycle when it is electrically least sensitive to interference with its functioning.

It is a further object of this invention to provide such a laser system which substantially reduces the chance of inducing fibrillation.

It is a further object of this invention which provides such a laser system which is safe, requires no attachment of the patient to a heart-lung machine, no cooling of the heart, and no opening of the sternum.

It is a further object of this invention to provide such a laser system which requires only a simple incision between the patient's ribs and results in less trauma, faster recovery and less blood loss.

It is a further object of this invention to provide an improved laser handpiece for a laser system for transmyocardial vascularization.

It is a further object of this invention to provide such a laser handpiece which more readily maintains perpendicularity with the wall of a beating heart.

It is a further object of this invention to provide such a laser handpiece which accurately locates the laser beam focal point at the correct point on the heart wall.

It is a further object of this invention to provide such a laser handpiece which reduces interference with the heart electric field and function.

It is a further object of this invention to provide such a laser hand piece which prevents interference with or damage to the laser beam lens.

It is a further object of this invention to provide such a laser handpiece which prevents movement of the handpiece with respect to the heart wall.

The invention results from the realization that a pulsed laser system can be achieved for operating on a beating heart accurately, with minimal interference to the heart and minimal risk to the patient by synchronizing the pulsing of the laser to the ECG of the heart so that laser pulses can be administered to the heart only during the moment when the heart is most still, least sensitive electrically, during the period between the R and the T waves of the ECG.

This invention features a heart-synchronized pulsed laser system including a laser system. There are means for sensing the contraction and expansion of a beating heart which is to be synchronized with the laser. There are means, responsive to the means for sensing, for generating a trigger pulse in response to the ECG signal, as well as means for positioning the leading edge of the trigger pulse during the contraction and expansion cycle of the heartbeat, and means for defining the width of a trigger pulse to occur during the heartbeat cycle. There are means responsive to the trigger pulse for firing the laser to strike the beating heart at the selected time indicated by the trigger pulse position and for the period indicated by the width of the trigger pulse.

In a preferred embodiment, the means for sensing the contraction and expansion includes means for sensing the ECG signal of the beating heart. There is a laser delivery system which may include an articulated beam delivery arm or a fiber optic element. The means for sensing the ECG signal of the beating heart may be an ECG unit and the means for generating the trigger pulse may do so in response to the R wave of the ECG. In the means for positioning, the leading edge of the trigger pulse may position the trigger pulse between the R and the T waves of the ECG. The means for defining the pulse width of the trigger pulse may define a pulse width which occurs in the period between the R and the T waves of the ECG.

The means for generating may include a marker pulse circuit for generating a specific time in a heartbeat cycle of the ECG for providing a marker pulse representative of that time. The means for generating may further include a trigger pulse circuit responsive to the marker pulse circuit for providing a trigger pulse whose position in the heartbeat cycle is a function of the specific time in the cycle represented by the marker pulse. The trigger pulse circuit may include means for delaying the marker pulse to locate it at a selected position relative to its initial position in the heartbeat cycle, and means for adjusting the duration of the marker pulse to a selected time to create the trigger pulse of the selected position and width.

The means for firing may include gate means for inhibiting delivery of the trigger pulse to the laser and may further include switch means for enabling the gate means to deliver the trigger pulse to the laser. There may be an arming circuit for further inhibiting delivery of the trigger pulse to the laser, and arming switch means for enabling the arming circuit to deliver the trigger pulse to the laser.

The handpiece of this invention results from the realization that an effective and safe handpiece capable of contacting the wall of the beating heart to insure proper location and focus of the laser beam, yet minimize danger to or interference with the beating heart, can be achieved by focusing the laser beam in the vicinity of the laser beam exit aperture at the end of the handpiece and providing a large, flat, knurled heart contact surface at the end of the handpiece and providing a large, flat, knurled heart contact surface at the end of the handpiece to minimize pressure on and interference with the beating heart and also to prevent movement of the contact surface with respect to the heart.

This invention features a handpiece for use in a medical laser system such as a transmyocardial revascularization heart-synchronized pulsed laser system as disclosed in U.S. Pat. Nos. 5,125,926 and 5,109,388.

The handpiece includes a barrel having a passage for transmitting a laser beam. A contacting wall is located on one end of the barrel to be positioned against the heart wall. The contacting wall includes an aperture in communication with the laser beam passage in the barrel. The contacting wall includes a solid face extending radially outward from the aperture to the periphery of the contacting wall providing a broad, flat contact surface for the handpiece which does not interfere with the function of the heart during the medical procedure and which stabilizes the handpiece on the heart wall. The contacting wall includes a knurled surface for preventing movement of the contacting wall with respect to the heart wall during surgery.

The barrel may include a window proximate the contacting wall and a finger grip along the length thereof to assist the surgeon in viewing the lasing site and to provide a firm grip during surgery.

The barrel may be straight or angled and include reflecting means such as a mirror. Also, a lens focusing unit may be included to focus the laser beam proximate the aperture, beyond the aperture, within the barrel, or in the aperture.

DISCLOSURE OF PREFERRED EMBODIMENT

Other objects, features and advantages will occur to those skilled in the art from the following description of a preferred embodiment and the accompanying drawings, in which.

Figure 2:
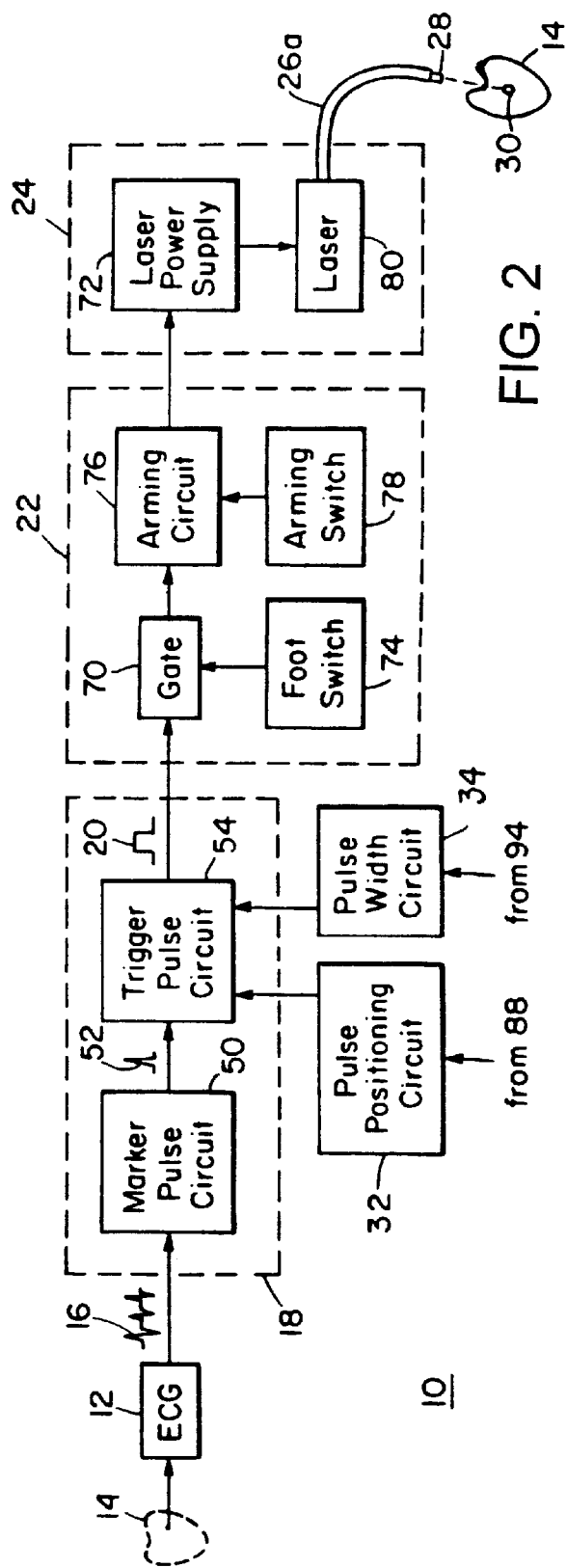
FIG. 2 is a more detailed diagram of the system of FIG. 1.
Figure 5A:
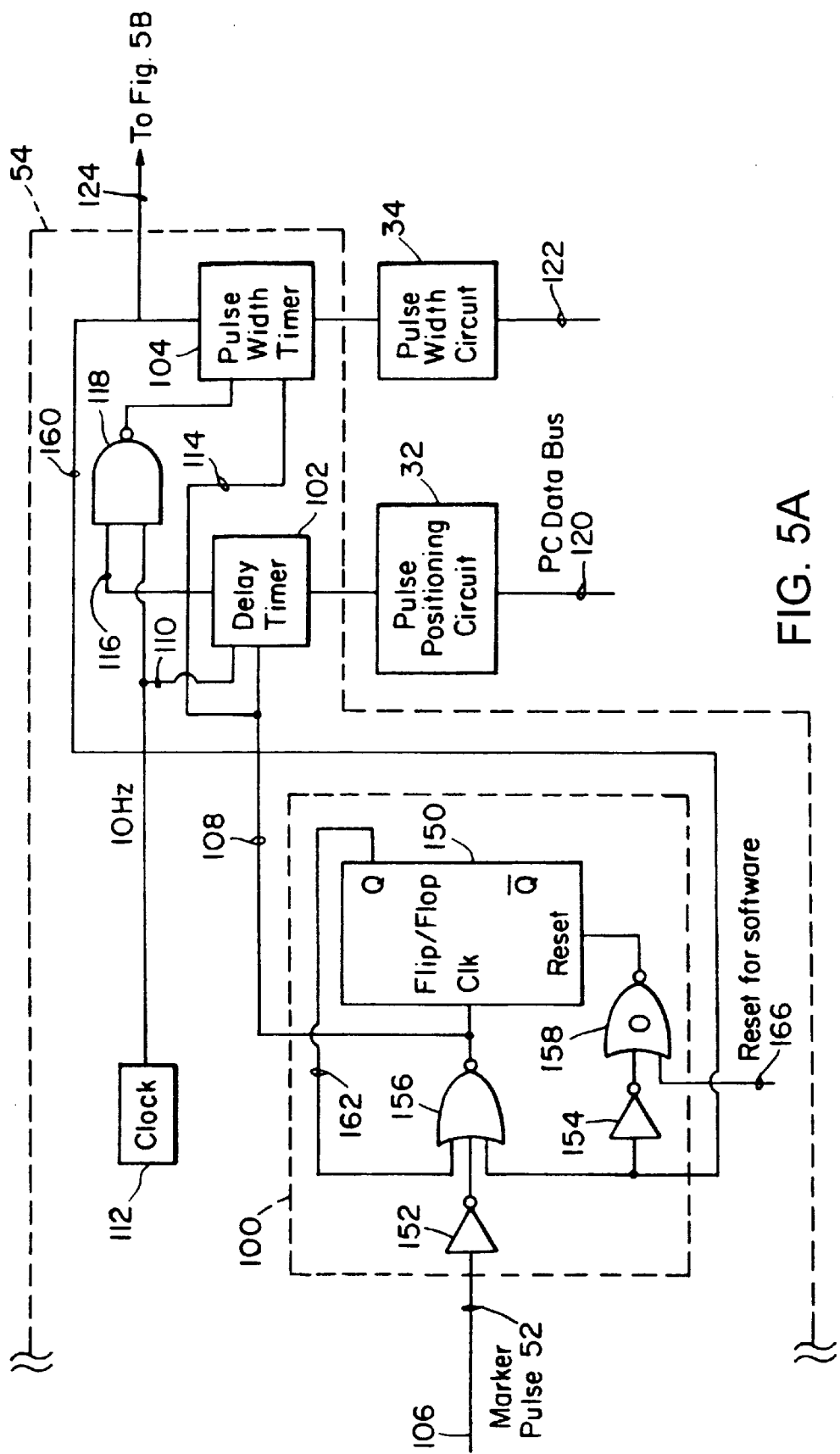
Figure 5B:
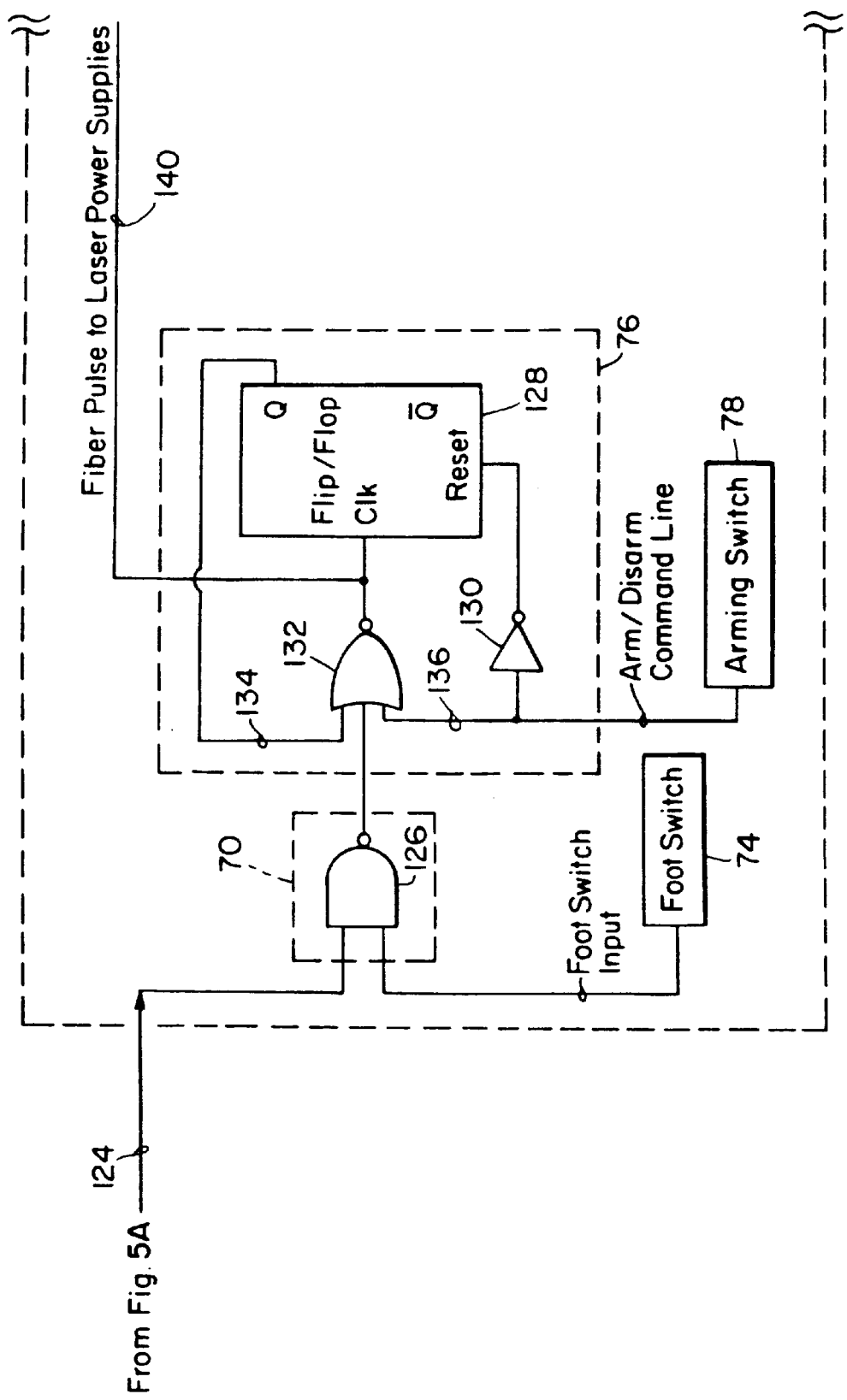
Figure 6:
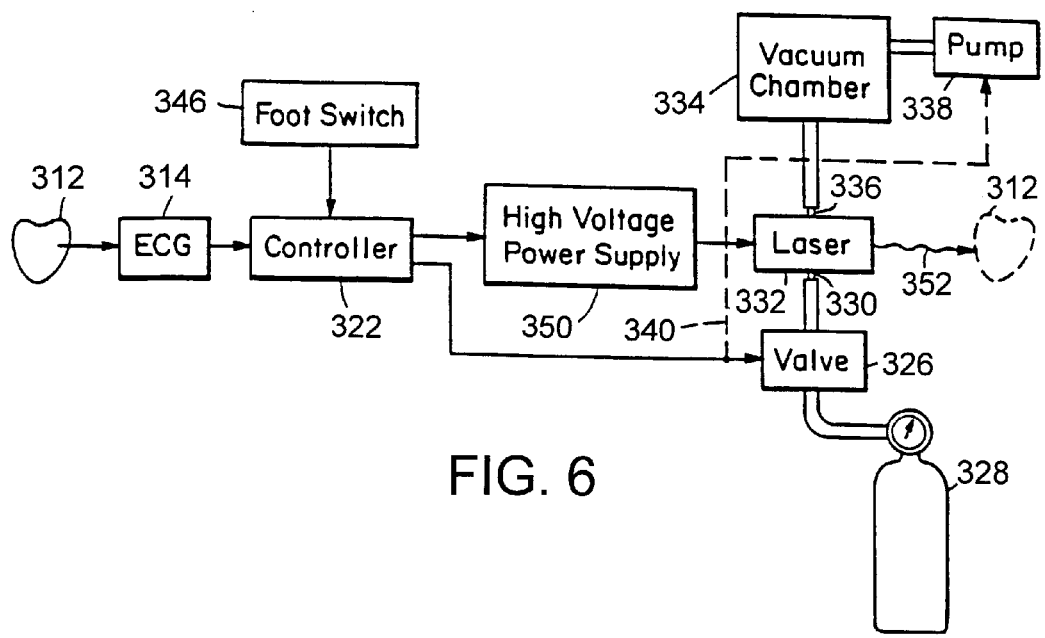
Figure 7:
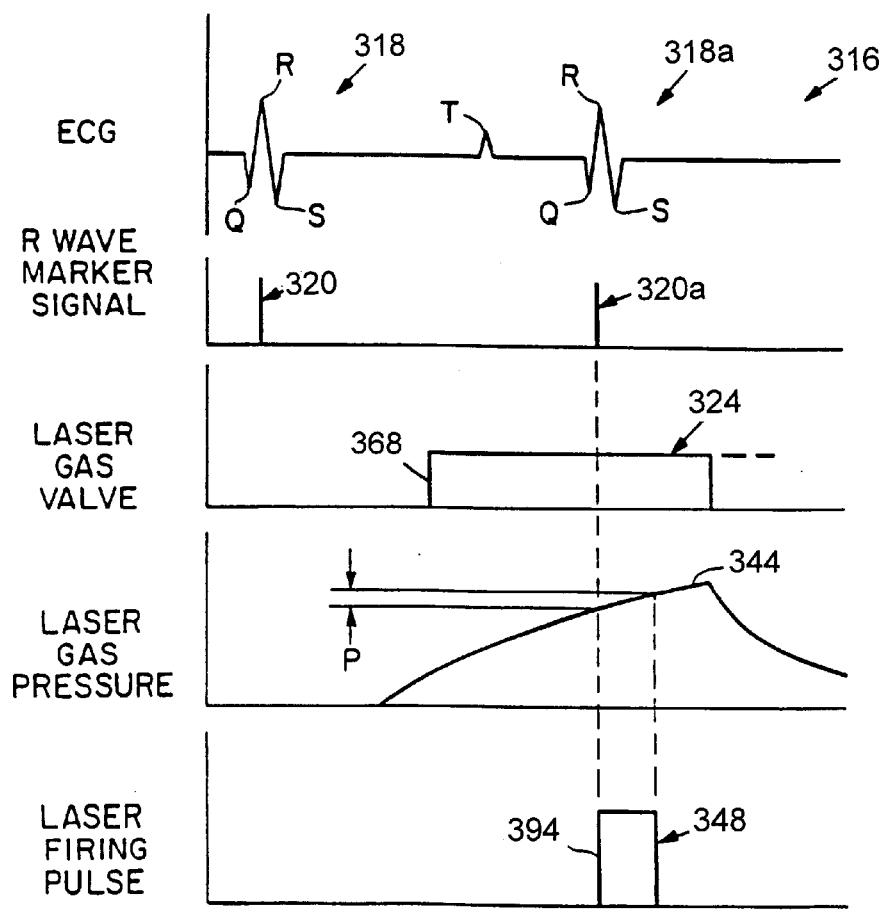
Figure 8:
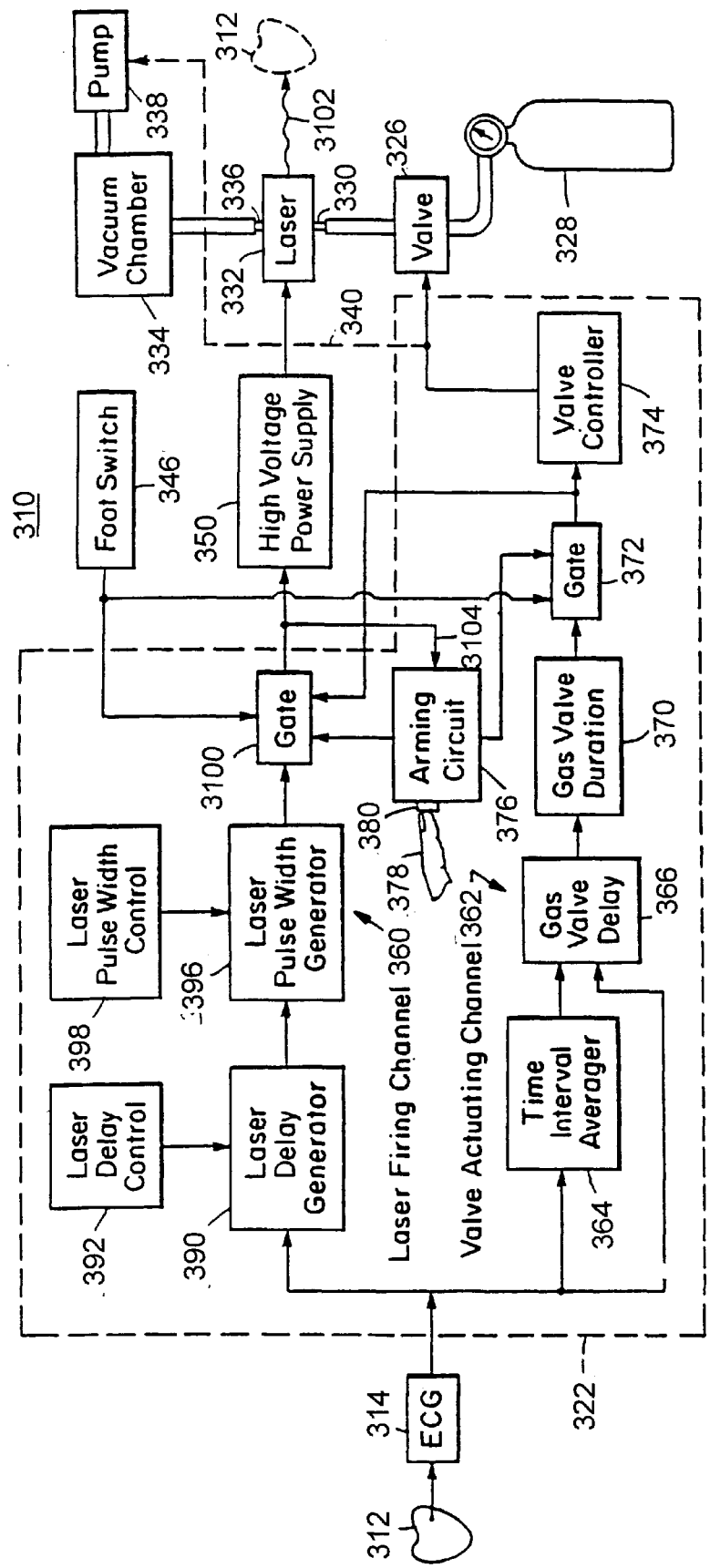
Figure 9:
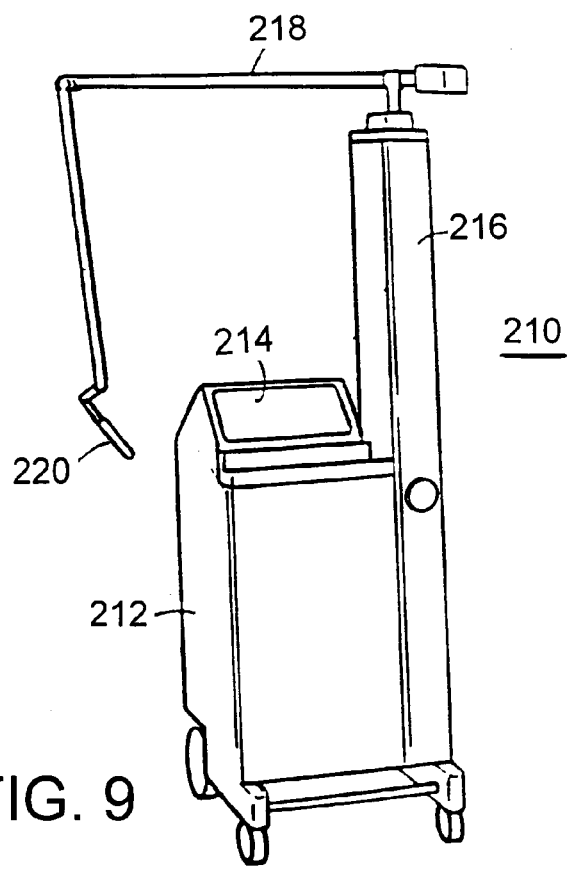
Figure 10:
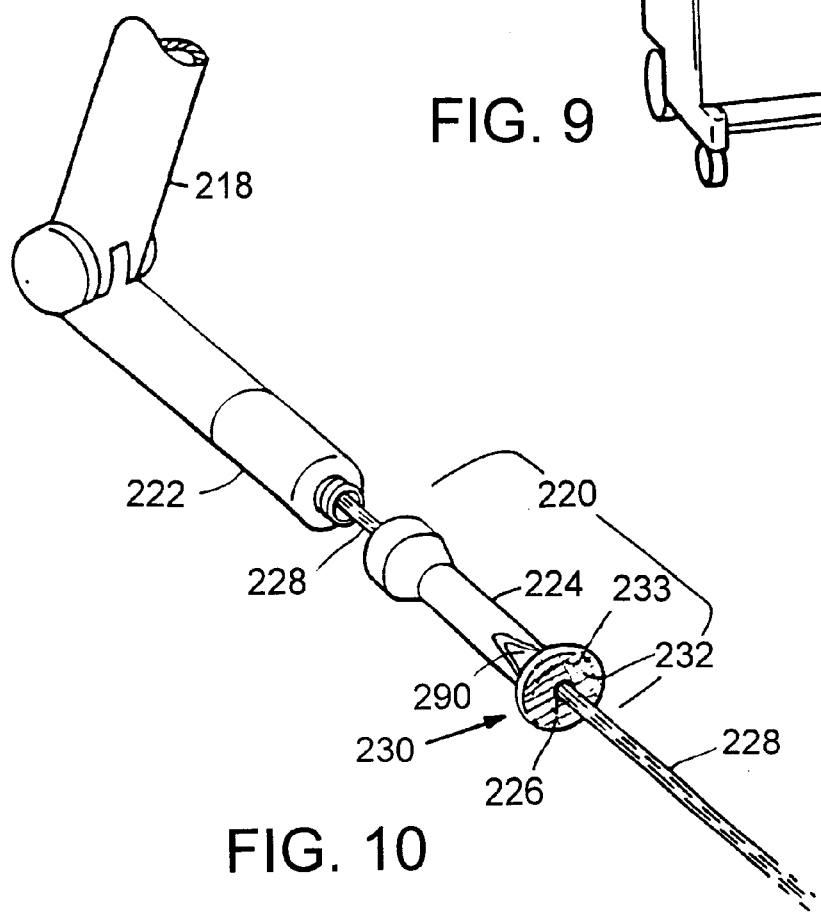
Figure 14:
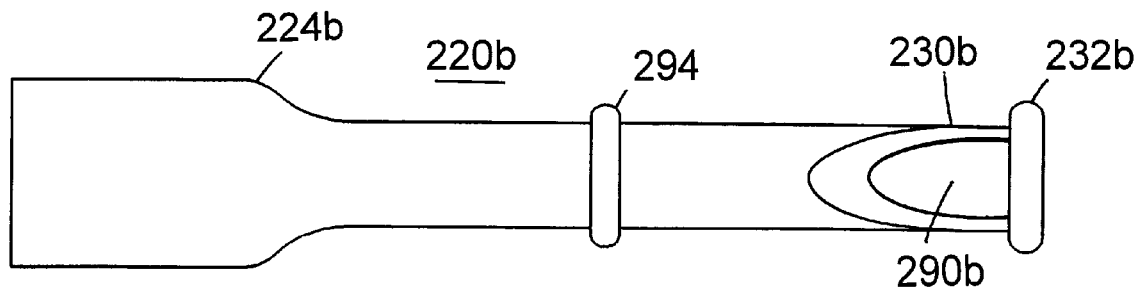
Figure 15:
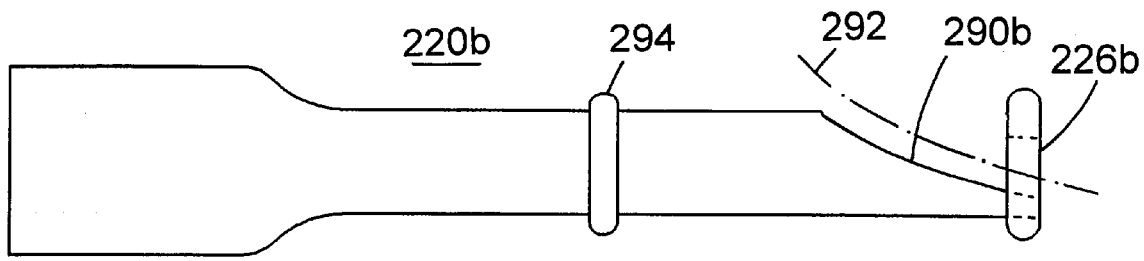
Figure 18:
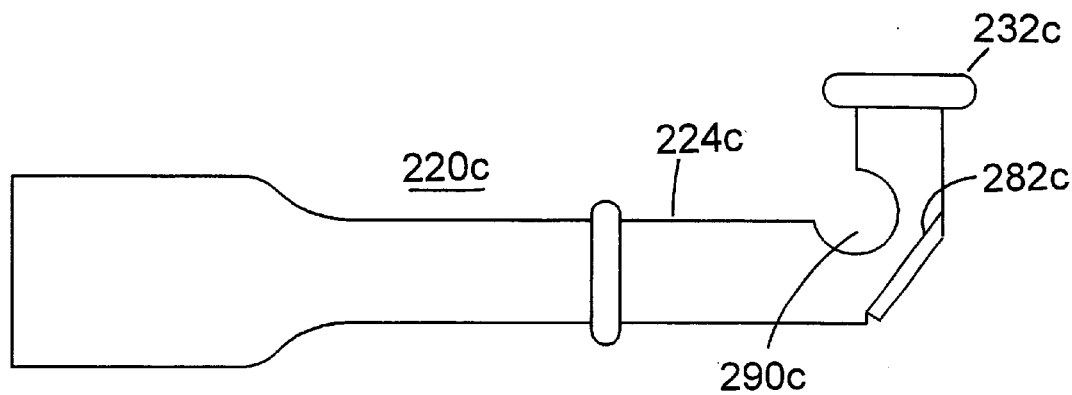
Figure 16:
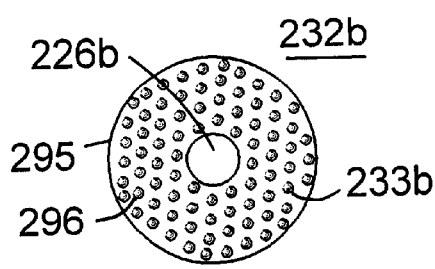
Figure 17:
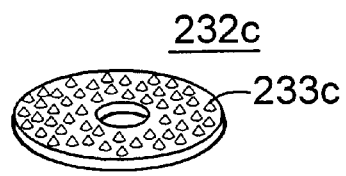

FIGS. 5A and B are more detailed schematic diagrams of the trigger pulse circuit, pulse positioning circuit, pulse width circuit and laser firing circuit of FIG. 2;

FIG. 6 is a simplified block diagram of a heart-synchronized vacuum assisted pulsed laser system according to the invention;

FIG. 7 is an illustration of wave forms occurring at various points in the system of FIG. 6;

FIG. 8 is a more detailed schematic diagram of the controller in FIG. 6;

FIG. 9 is a three-dimensional view of a $CO_2$ surgical laser system employing the handpiece of this invention;

FIG. 10 is an enlarged view of a handpiece according to this invention and a portion of the articulated optical arm which carries it;

FIG. 11 is an enlarged cross-sectional view of the focusing lens assembly incorporated with the handpiece of FIGS. 9 and 10;

FIG. 12 is an enlarged sectional view of the barrel of the handpiece of FIGS. 9 and 10;

FIG. 13 is a side elevational view with portions broken away of an alternative form of barrel similar to that shown in FIG. 12;

FIG. 14 is a top view of another embodiment of the handpiece according to this invention;

FIG. 15 is a side view of the handpiece of FIG. 14;

FIG. 16 is an end view of the contacting wall of the barrel of FIG. 14 showing the knurled surface;

FIG. 17 is a schematic three-dimensional view of another embodiment of the knurled contacting wall for the handpiece according to this invention; and FIG. 18 is a sideview of an angled barrel for a handpiece according to this invention.

This invention may be accomplished in a heartsynchronized pulsed laser system having a laser and a laser beam delivery system. The laser is typically a pulsed 50 Joules $CO_2$ laser. The laser beam delivery system may be an articulated optical arm or a fiber optic element with a suitable handpiece or terminal optics at the distal end for delivering the laser beam for perforating the heart. There is some means for sensing the electrocardiogram signal of the beating heart to be synchronized with the laser. This may be a standard ECG device such as obtainable from Hewlett-Packard Company. The system uses some means for generating a trigger pulse in response to the ECG signal. Typically the trigger pulse is a function of the R wave of the heartbeat cycle generated by the conventional ECG equipment. The heartbeat cycle has four distinct waveforms, the Q, the R, the S, and the T. There are means for setting the beginning of the trigger pulse so that it occurs in the proper time relationship to the R wave and ends before the T wave to avoid interference with the electrical characteristics of the beating heart. The pulse positioning circuit locates the leading edge of the trigger pulse and a pulse width circuit determines the width so that it extends over only the necessary and safe duration of the heartbeat cycle. The trigger pulse is passed to a laser firing circuit, which then operates the laser to produce a pulsed laser beam to the delivery system which the surgeon aims precisely at the beating heart preferably during the time between the R and T waves of the heartbeat cycle where the heart is most static, and the accuracy is most assured.

The trigger generator may include a marker pulse circuit for detecting a specific time in the heartbeat cycle of the ECG signal and providing a marker pulse representative of that time. The time may be when the R wave crosses a particular threshold or some time related to that time. The marker pulse circuit may be built in as a part of the readily obtainable ECG unit such as a type HP78352A obtainable from Hewlett-Packard Company. The trigger pulse circuit, also is the means for generating the trigger pulse, responds to the marker pulse circuit to provide a trigger pulse whose position in the heartbeat cycle is a function of that specific time in the cycle represented by the marker pulse. The trigger pulse circuit typically includes means for delaying the marker pulse to locate it at a selected position relative to its initial position in the heartbeat cycle, and also contains means for adjusting the delay of the marker pulse to a selected time to create the trigger pulse of the selected position and width. The position of the trigger pulse and its width may be adjusted by a pulse positioning circuit and a pulse width circuit. The laser firing circuit includes a gate which inhibits delivery of the trigger pulse to the laser unless a foot switch is enabled by the surgeon when he is ready to make a hole in the heart. There is also an arming circuit which further inhibits delivery of the trigger pulse to the laser, even if the surgeon steps on the foot switch unless that arming switch has been actuated. If the arming switch is actuated and the foot switch is depressed, the next trigger pulse will be directed to fire the laser and provide a pulsed laser beam.

Figure 1:
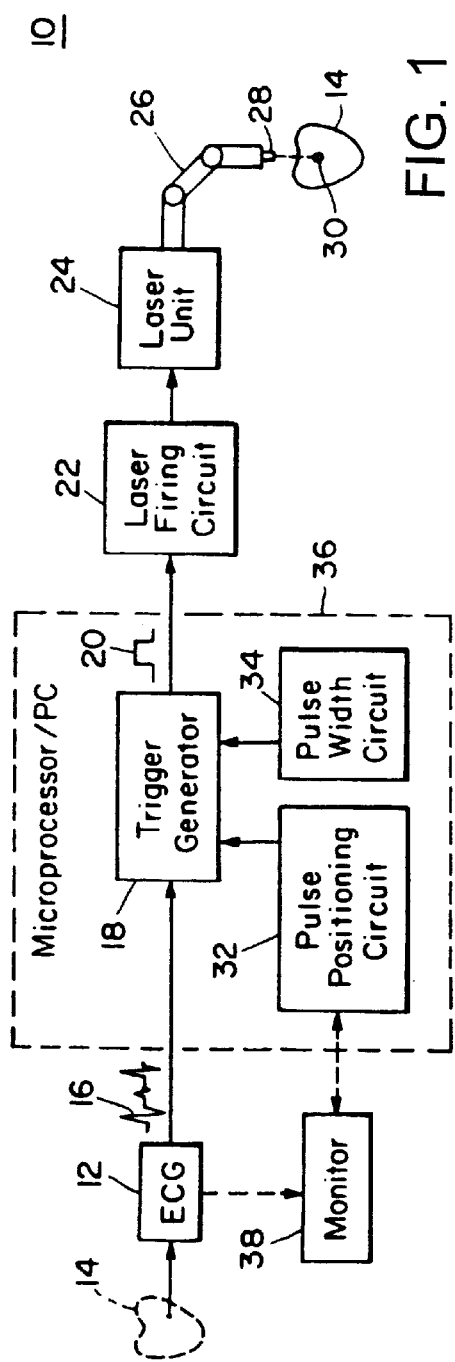
FIG. 1 is a schematic block diagram of a heart-synchronized pulsed laser system according to this invention.

There is shown in FIG. 1 a heart-synchronized pulsed laser system 10 with electrocardiogram unit 12 connected to a heart 14 which is to undergo the surgery. The ECG signal 16 is delivered to trigger generator 18, which provides a trigger pulse 20 to laser firing circuit 22, which in turn energizes laser unit 24 including a laser power supply and a laser to produce a pulsed laser beam through articulated optical arm 26 into optical handpiece 28 to make a hole 30 in heart 14. The position of trigger pulse 20 in the heartbeat cycle of ECG signal 16 is determined by pulse positioning circuit 32. The width of the pulse 20 and its duration during the heartbeat cycle is determined by pulse width circuit 34. Trigger generator 18 as well as pulse positioning circuit 32 and pulse width circuit 34, may be included as an additional board in a PC or a microprocessor 36, in which case the system can be controlled through the computer keyboard and suitable software. PC 36 and ECG 12 may have separate monitors, or they may have a single monitor 38 which displays both the ECG and information about the trigger pulse 20. Trigger generator 18 may include a marker pulse circuit 50 which provides marker pulse 52 and trigger pulse circuit 54 which responds to marker pulse 52 to create trigger pulse 20. Alternatively, marker pulse circuit 50 is included in the ECG itself in some cases.

Figure 3:
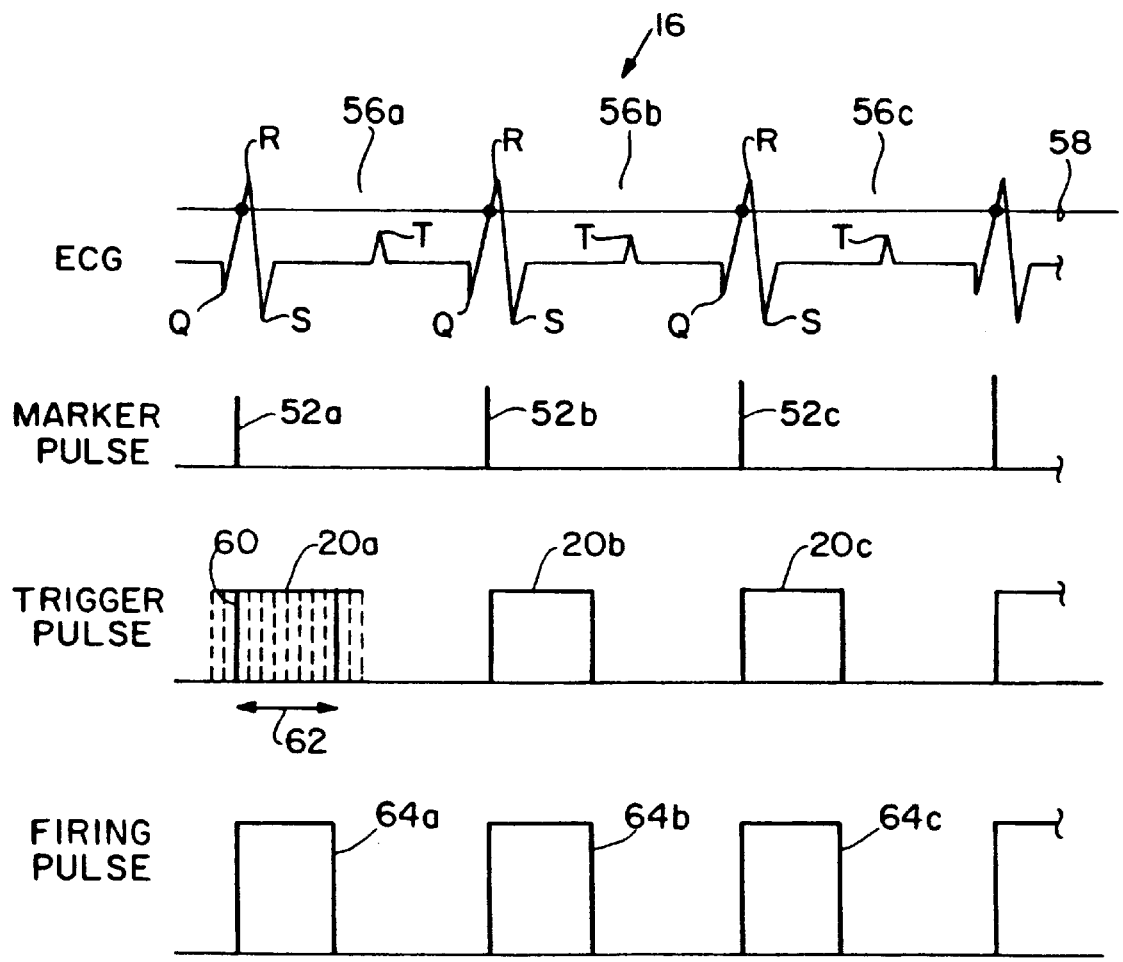
FIG. 3 illustrates the ECG signal, marker pulse, trigger pulse and firing pulse waveforms occurring in the heartsynchronized pulsed laser system described in FIGS. 1 and 2.

This can be better understood with reference to FIG. 3, where ECG signal 16 may be seen as consisting of a series of heartbeat cycles 56a, 56b, 56c each of which contains the waveforms Q, R, S and T. Where waveform R crosses preselected threshold 58, marker pulses 52a, 52b, 52c are created. Trigger pulses 20a, 20b, 20c are then created by trigger pulse circuit 54. The position of the leading edge 60 and the overall width 62 of each trigger pulse 20 is determined, respectively, by pulse positioning circuit 32 and pulse width circuit 34. In response to trigger pulse 20, a firing pulse 64 indicated as 64a, 64b and 64c, FIG. 3, is created to energize laser 24.

In FIG. 2, laser firing circuit 22 is shown to include gate 10 which generally inhibits the delivery of trigger circuit 20 to laser power supply 72 in laser unit 24. The inhibiting effect of gate 70 can be overcome when the surgeon steps on foot switch 74. Trigger pulse 20 is still inhibited, however, by arming circuit 76 which in turn can have its inhibiting effect overcome by the operation of arming switch 78. This double lock on the delivery of trigger pulse 20 to laser power supply 72 ensures that the firing of the laser is truly desired and not accidental. Thus the surgeon must first arm the system by operating arming switch 78 to enable arming circuit 76. Then and only then is he able to pass the next occurring trigger pulse 20 through gate 70 to the laser power supply 72 by actuating his foot switch 74. Also included in laser unit 24 is a standard CO laser 80. The output of laser 80 may be delivered through a fiber optic element 26a to handpiece 28.

Figure 4:
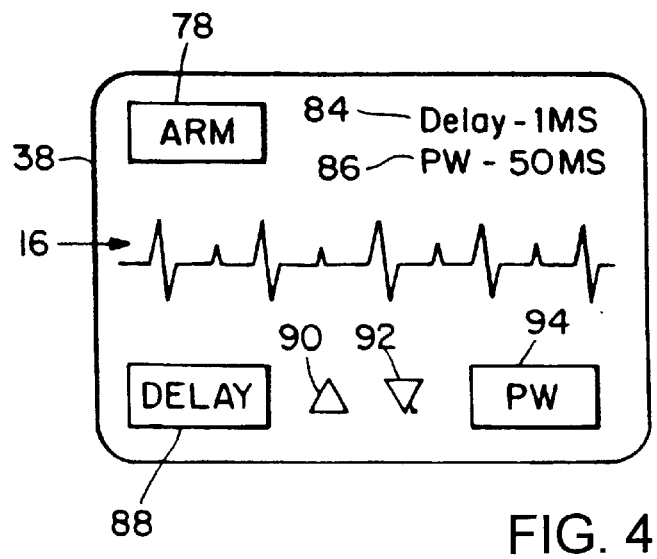
FIG. 4 is an illustration of a touch-sensitive monitor that may be used in conjunction with the system of FIGS. 1 and 2.

Monitor 38, FIG. 4, may display both the ECG signal 16 and the display of the delay 84 which has been introduced by pulse positioning circuit 32, FIG. 2, which delay is indicated as one millisecond in FIG. 4. It may also include the pulse width 86 shown as 50 milliseconds selected by the pulse width circuit 34, FIG. 2. Monitor 38 may also include a delay selection switch 88 which when pressed enables one to increase or decrease the delay time by simply touching the up 90 or down 92 arrows on the screen. Pulse width touch switch 94 may be used in the same fashion to adjust the pulse width duration.

Trigger pulse width circuit 54, FIG. 5A may include an anti-false trigger pulse circuit 100 which prevents a false firing or second firing of the system when a firing sequence is already in progress. Also included in trigger pulse circuit 54 is a delay timer 102 and a pulse width timer 104. When marker pulse 52 on line 106 is permitted to pass through anti-false trigger pulse circuit 100, the marker pulse is input on line 108 to delay timer 102. The conjunction of the marker pulse with the input on line 110 from 10 KHz clock 112 causes delay timer 102 to set the position of the leading edge of the trigger pulse. The appearance of the marker pulse on line 108 also is delivered as an enable signal on line 114 to preset pulse width timer 104. When the leading edge position of the trigger pulse has been set by delay timer 102 a signal is provided on line 116 to AND gate 118, which in conjunction with a signal from clock 112 causes the trigger pulse to be expanded to a predetermined width in pulse width timer 104. The specific positioning of the leading edge of the trigger pulse by delay timer 102 is controlled by pulse positioning circuit 32 which is typically a time delay data latch under control of the computer via the data bus 120. Similarly, the duration of the pulse imparted by pulse width timer 104 is controlled by pulse width circuit 34, typically a pulse width time data latch under control of the microprocessor or PC via bus 122. The trigger pulse then is delivered over line 124 to gate 70 which may include simply and AND gate 126.

Arming circuit 76 includes flip-flop 128, inverter 130, and OR gate 132. When arming switch 78 is actuated, the signal to inverter 130 resets flip-flop 128 SO that now there is a proper output on line 134 from flip-flop 128 into OR gate 132 as well as the proper input from arming switch 78 on line 136 into OR gate 132. Thus, when next the trigger pulse arrives on line 124, if the doctor operates the foot switch 74 the pulse will be passed through AND gate 126 and OR gate 132 to pass the trigger pulse on line 140 to laser power supply 72. When the trigger pulse passing through OR gate 132 ends, the clock input to flip-flop 128 is no longer enabled and the output on line 134 ceases so that OR gate 132 is no longer enabled to pass subsequent trigger pulses to line 140 and laser power supply 73.

The anti-false trigger pulse circuit 100 uses a flip-flop 150, two inverters 152 and 154, and two OR gates 156 and 158. Then a trigger pulse is supplied on line 124 by pulse width timer 104, it is also simultaneously placed on line 160 which is connected to inverter 154 and to OR gate 156. At the end of the trigger pulse, the proper level appears on line 160 to enable OR gate 156 and to reset flip-flop 150 through inverter 154 and OR gate 158. When flip-flop 150 is reset it provides a second enabling input on line 162 to OR gate 156. Thus when next a marker pulse 52 is delivered on line 106 and passed by inverter 152 to OR gate 156, it is passed to line 108 and thus on to delay timer 102. The marker pulse 52 appearing on line 108 also clocks flip-flop 150 so that the proper signal is no longer on line 162 and AND gate 156 is disabled. Until a reset occurs from the software on line 166 or the end of the trigger pulse level occurs on line 160 no further marker pulses will be passed.

There is shown in FIG. 6 a heart-synchronized vacuum pulsed laser system 310 according to this invention. The patient whose beating heart is to be operated on is connected to an electrocardiogram unit 314 which provides the electrocardiogram 316, FIG. 7, that includes recurring heart cycles 318, 318*a* including Q, R, S and T waves. This electrocardiogram signal, or preferably simply the R wave marker signal 320, FIG. 7, is delivered to controller 322, FIG. 6. The controller constantly determines the average period of the heart wave cycles 318, 318*a*, or preferably the period between R wave marker signals 320, 320*a*. From this controller 322 determines the proper time to trigger the laser gas valve signal 324, FIG. 7, which operates valve 326, FIG. 6. A suitable ECG unit is a Model HP 78352A made by Hewlett-Packard Company. When valve 326 is actuated it permits the laser gas, which is a mixture of helium, carbon dioxide and nitrogen, typically under a pressure of 60 psi, to be delivered from laser gas source 328 to laser gas inlet 330 of $CO_2$ laser 332. Pressurized laser gas flows through laser 332 assisted by the draw of the vacuum in vacuum chamber 334 which is connected to laser gas outlet 336. The vacuum chamber 334 is maintained by a pump 338. The duration of the operation of valve 326 is so short that pump 338 may be set to simply respond to a decrease in the vacuum in vacuum chamber 334 to energize and attempt to reestablish the vacuum. Or, when the actuating signal to valve 326 is ceased, that change in condition may be reflected over line 340 to pump 338 to command it to begin pumping only after the valve 326 has once again closed. In either case, the laser gas valve 324, FIG. 7, is timed so that the laser gas pressure reaches a pressure range, P, as indicated by the laser gas pressure wave 344, FIG. 7, such as 50 to 150 torr, during the occurrence of the R wave or R wave marker signal 320. At this point, provided the surgeon has operated foot switch 346, a laser firing pulse 348, FIG. 7, is generated by controller 322 and directed to high-voltage power supply 350, which fires lasers 332 during the period when the laser gas pressure is in the range P and produces a laser beam 352 which strikes beating heart 312 at precisely the right moment proximate the occurrence of the R wave.

Controller 322 includes a laser firing channel 360 and a valve actuating channel 362. Valve actuating channel 362 includes a time interval averager circuit 364, which determines the average time from R wave to R wave in the heart cycles of the ECG. This signal, together with the R wave marker signal itself, is delivered to gas valve delay circuit 366. It is this circuit which determines the start time for the leading edge 368 of laser gas valve signal 324, FIG. 7, which is empirically determined to provide sufficient time for the laser gas pressure wave 344 to reach the proper range P of pressure at the time the R wave occurs. The duration of the laser gas valve signal 324 is determined by gas valve duration circuit 370, which keeps valve 326 open long enough to gain the desired pressure range P, and then shuts off valve 326 after the laser has been fired to enable the vacuum in chamber 334 to be reconstituted by pump 338. Each time a marker pulse is sensed, valve actuating channel 362 provides the laser gas valve signal 324 to gate 372. However, gate 372, only passes that signal to valve controller circuit 374, which then operates valve 326, if gate 372 has received two signals: one from the actuation of foot switch 346 by the surgeon, the other from arming circuit 376, which may be operated for example by simply pressing a finger 378 against an actuator button 380. The arming circuit ensures that accidental operation of the foot switch will not cause the system to fire a laser beam at the heart.

At the same time that the ECG signals or R wave marker signals are being delivered to channel 362, they are also being delivered to laser firing channel 360. There, laser delay generator circuit 390, under control of laser delay control circuit 392, sets the position of the leading edge 394, FIG. 7, of the laser firing pulse 348 so that it occurs coincident with or approximately coincident with the R wave or R wave marker signal 320. The width of laser firing pulse 348 is set by laser pulse width generator circuit 396 under control of the laser pulse width control circuit 398. The width is set to provide sufficient energy in the a laser beam to puncture the wall of the heart undergoing the surgery. Laser pulse 348, like laser gas valve signal 324, is generated at each heart cycle upon the occurrence of the R wave or the R wave marker signal. However, it will not be passed by gate 3100 unless that gate is enabled. Gate 3100 is enabled by the coincidence of three signals: one from foot switch 346, one from arming circuit 376, and a third from the output of gate 372 indicating that the valve 326 has been opened and gas flow has been established through laser 332. When all of these events occur, gate 3100 is enabled to pass laser firing pulse 348 to high-voltage power supply 350, which then in turn fires laser 332 and produces the beam 3102 which strikes heart 312. As soon as the laser firing pulse 348 is passed by gate 3100, a signal is delivered on line 3104 to disable arming circuit 376 so that the system cannot be fired again by merely holding down the foot switch: the arming circuit must be newly actuated before foot switch 346 is again functional.

The handpiece of this invention for use in a transmyocardial revascularization heart-synchronized pulsed laser system may be accomplished using a barrel having a passage for transmitting a laser beam. The barrel may be simply a hollow tube. There is a surface at the distal end of the barrel for contacting the wall of the heart. This surface is broad and flat so that there are no sharp points to probe or prick the heart wall. This shape also minimizes the contact pressure between the handpiece and the heart wall and minimizes interference with the operation of the heart muscle and the electrical activity of the beating heart. The handpiece, at least at its contact surface, is electrically and thermally insulating for the same purpose. There is an aperture located at the distal end of the barrel in the enlarge surface for transmitting a laser beam through to the heart wall. There are also some means for focusing the laser beam proximate to the aperture to vaporize the tissue of the heart wall and create a hole through the wall to the interior of the heart chamber. The means for focusing is typically a lens which is mounted in a focusing unit or lens unit associated with the barrel.

The laser may be focused at, near or beyond the aperture. There is an inlet to introduce a purging gas through the passage to purge the aperture and the means for focusing of debris produced by the vaporization of the heart wall by the laser beam. There is one or more outlets proximate the distal end of the barrel through which the purged gas with the debris is vented. The barrel may be straight or may be angled. If it is angled, there are suitable deflecting means such as mirrors or reflectors, to redirect the beam along the angled or curved barrel. The contacting wall is knurled for preventing movement of the contacting wall with respect to the heart wall during surgery. By "knurled" is meant any frictional surface.

There is shown in FIG. 9 a surgical laser system 210 including a power supply 212 and control panel 214 for operating $CO_2$ laser 216 whose output beam is directed through articulated arm 218 to handpiece 220. Handpiece 220, FIG. 10, may be connected to lens unit 222 including a lens for focusing the laser beam. Barrel 224 of handpiece 220 includes an aperture 226 through which the laser beam 228 exits. The distal end 230 of barrel 224 includes an enlarged knurled contacting wall 232 for contacting the wall of the heart to be perforated by the laser beam. Contacting wall 232 is relatively large to minimize the contact pressure between it and the heart wall, and is flat with rounded edges to minimize interference with the heart. Contacting wall 232 includes knurled surface 233 for preventing movement of contacting wall 232 with respect to the heart wall during surgery. Contacting wall 232 is typically 1 cm or greater in diameter, and may be electrically and thermally insulating.

Window 290 allows the surgeon to view the lasing site and also serves to vent gasses and vapor. Focusing unit or lens unit 222, FIG. 11, includes a threaded portion 240 which interconnects with barrel 224 of handpiece 220. Carried within unit 222 is focusing lens 242. An inlet tube 244 in joined by interference fit with bore 246 and a cylindrical wall 248 of unit 222. At its free end 250, inlet 244 is connected to a hose 252 which is in turn connected to a purge gas source 254 which provides a gas such as $CO_2$ under gentle pressure to create a backflow from lens 242 forward into barrel 224. This keeps any debris from the vaporization from contacting and obscuring or damaging lens 242. Lens 242 is positioned directly in line with passage 256 provided in unit 222 for propagation of the laser beam. Threads 240 of lens unit 222 engage with threads 260 of barrel 224, FIG. 12, which also includes a passage 262 which communicates with laser aperture 226 to create a clear passage for the propagation of laser beam 228 to wall 266 of a beating heart. Other connection means may be used to engage lens unit 222 with barrel 224 such as snap on, or turn and lock type connections. Lens 242 focuses the laser beam 228 proximate aperture 226 and surface 232.

As can be seen clearly in FIG. 12, contacting wall 232 of handpiece 220 is considerably broader than the cross-sectional area of barrel 224 alone and is formed in the shape of a flange with knurled surface 233 being relatively flat and all the edges rounded. This increases the area of contact with the heart and therefore decreases the pressure of force per unit area on the heart. It also provides a more stable platform by which to maintain perpendicularity between the beam 228 and the heart wall 266. Thus, this construction provides the necessary precision in locating the focus of the beam on the heart wall without interfering with the heart operation or its electrical activity. Barrel 224 may include vent holes 270, 272 for exhausting the purging gas and trapped debris away from the lens 242 and away from aperture 226.

Although handpiece 220 has been shown with barrel 224 as a straight member, this is not a necessary limitation of the invention. For example, barrel 224a, FIG. 13, may include a right angle configuration 280, so that contacting wall 232a is facing at a right angle to the path of the laser beam. A reflective surface 282 is provided to reflect the beam from an incoming path parallel to axis 284 to the outgoing path parallel to axis 286. One or more vent holes 288 may be provided for exhausting gas. Angles other than a right angle are possible for barrel 224a.

In another embodiment, handpiece 220b, FIG. 14 includes barrel 224b with contacting wall 232b on distal end 230b of barrel 224b. Window 290b is proximate contacting wall 232b for vapor release and also so that surgeon can view the site being lased. As shown in FIG. 15, the surgeon has a clear view of the lasing site proximate aperture 226b through window 290b along axis 292. Raised rim 294 on barrel 224b provides a finger grip for the surgeon to assist in gripping barrel 224b.

Contacting wall 232b, FIG. 16, includes knurled surface 233b formed by cross hatching surface 233b as shown, while in another embodiment, contacting wall 232c, FIG. 17, includes knurled surface 233c consisting of a series of raised ridges. Other surface patterns are possible and are within the scope of this invention. And, although the entirety of wall 232b has the rough "knurled" appearance, this is not a limitation of the present invention since only half, or some other portion may be knurled. Contacting wall 232b, FIG. 16, includes solid face 296 which extends continuously radially outward from aperture 226b to the periphery 295 of contacting wall 232b.

Right angled barrel 224c of handpiece 220c, FIG. 18 includes contacting wall 232c facing at a right angle to the path of the laser beam. Reflective surface 282c, such as a mirror, reflects the beam as discussed with reference to FIG. 13. Window 290c is provided for cleaning reflective surface 282c and provides an aperture from which purge gasses and debris are evacuated from barrel 224c.

In a preferred embodiment, the handpiece is manufactured from a medical grade acrylic and is injection molded to form the different barrel shapes.

Although specific features of the invention are shown in some drawings and not others, this is for convenience only as each feature may be combined with any or all of the other features in accordance with the invention.

And other embodiments will occur to those skilled in the art and are within the following claims.

What is claimed is:

1. A heart-synchronized energy delivery system for performing myocardial revascularization on a beating heart of a patient comprising:
   an energy pulse system that produces energy pulses sufficient to create channels in a wall of said beating heart;
   a sensor that senses a cyclical event related to the contraction and expansion of said beating heart; and
   an energy pulse system controller responsive to said sensor for firing said energy pulse system to provide energy to strike said beating heart only within a safe time period during a heart beat cycle, said safe time period being automatically determined by said controller with respect to said cyclical event.

2. The heart-synchronized system of claim 1 wherein said safe time period is a period in which firing of said energy pulse system will not cause fibrillation of the heart.

3. The heart-synchronized system of claim 1 wherein said safe time period is a period during which said heart is less sensitive electrically.

4. The heart-synchronized system of claim 1 wherein said sensor senses an electrical signal that causes said heart to beat.

5. The heart-synchronized system of claim 4 wherein said electrical signal is an ECG signal of said beating heart, said ECG signal including Q, R, S, and T waves.

6. The heart-synchronized system of claim 5 wherein said safe time period begins at or after the R wave and extends past the S wave.

7. The heart-synchronized system of claim 6 wherein said safe time period ends before the T wave.

8. The heart-synchronized system of claim 6 wherein said safe time period begins during the R wave.

9. The heart-synchronized system of claim 1 wherein said energy pulse system produces electromagnetic energy.

10. The heart-synchronized system of claim 9 wherein said laser is a $CO_2$ laser.

11. The heart-synchronized system of claim 9 wherein said energy pulse system includes a laser.

12. The heart-synchronized system of claim 11 wherein said laser provides a single continuous laser pulse within said safe time period of a heart beat cycle.

13. The heart-synchronized system of claim 11 wherein said laser provides constant laser energy during the time fired in said safe time period.

14. The heart-synchronized system of claim 11 wherein said energy pulse system includes a laser power supply that fires said laser.

15. The heart-synchronized system of claim 14 wherein said power supply is a high-voltage power supply.

16. The heart-synchronized system of claim 1 wherein said energy pulse system controller includes an operator input device that provides an activation signal to activate firing of said energy pulse system.

17. The heart-synchronized system of claim 16 wherein said energy pulse system controller fires said energy pulse system during said safe time period subsequent to receiving said activation signal.

18. The heart-synchronized system of claim 16 wherein said operator input device includes an operator activation switch.

19. The heart-synchronized system of claim 18 wherein said operator activation switch is a foot switch.

20. The heart-synchronized system of claim 1 wherein said energy pulse system includes an energy source and an energy pulse delivery system for delivering said energy pulses to a desired location for a said channel in a wall of said beating heart.

21. The heart-synchronized system of claim 20 wherein said energy pulse delivery system is sized to deliver said energy pulses through a small incision in said patient to said desired location of said heart wall.

22. The heart-synchronized system of claim 20 or 21 wherein said energy pulse delivery system delivers said energy pulses to an outside surface of a wall of said heart.

23. The heart-synchronized system of claim 20 or 21 wherein said energy pulse delivery system includes a handpiece.

24. The heart-synchronized system of claim 20 or 21 wherein said energy pulse delivery system includes a fiber-optic element.

25. The heart-synchronized system of claim 20 or 21 wherein said energy pulse delivery system includes a fiber-optic element and terminal optics at a distal end of said fiber-optic element.

26. The heart-synchronized system of claim 1 wherein said energy pulse system controller includes a trigger generator that is responsive to said sensor to generate a beginning signal at a time related to the occurrence of said cyclical event, and wherein said beginning signal is used to automatically determine the beginning of said safe time period.

27. The heart-synchronized system of claim 26 wherein said energy pulse system controller includes a delay circuit connected to said trigger generator to provide said beginning signal at a predetermined delay time with respect to said cyclical event.

28. The heart-synchronized system of claim 26 wherein said trigger generator generates a trigger pulse to provide said beginning signal.

29. The heart-synchronized system of claim 26 wherein said sensor provides an electrical signal conveying information about said cyclical event, and said trigger generator includes a threshold circuit to identify said cyclical event when said electrical signal meets a threshold condition.

30. The heart-synchronized system of claim 26 wherein said trigger generator provides an end signal to automatically determine the end of said safe time period.

31. The heart-synchronized system of claim 30 wherein said energy pulse system controller includes a time period duration circuit to provide said end signal at a predetermined delay time with respect to said beginning signal.

32. The heart-synchronized system of claim 30 wherein said trigger generator generates a trigger pulse to provide said end signal.

33. The heart-synchronized system of claim 30 wherein said trigger generator generates a trigger pulse with a leading edge and a trailing edge, said beginning signal being provided by said leading edge, said end signal being provided by said trailing edge.

34. The heart-synchronized system of claim 26 wherein said energy pulse system controller includes a firing circuit that is responsive to said trigger generator to provide a firing signal to fire said energy pulse system in said safe time period.

35. The heart-synchronized system of claim 34 wherein said energy pulse system controller includes an operator input device that provides an activation signal to said firing circuit.

36. The heart-synchronized system of claim 35 wherein said firing circuit fires said energy pulse system at said safe time period subsequent to receiving said activation signal.

37. The heart-synchronized system of claim 1 wherein the timing of said safe time period is adjustable by said energy pulse system controller.

38. The heart-synchronized system of claim 37 wherein the beginning of said safe time period is adjustable by said energy pulse system controller with respect to said cyclical event.

39. The heart-synchronized system of claim 37 wherein the end of said safe time period is adjustable by said energy pulse system controller with respect to the beginning of said safe time period.

40. The heart-synchronized system of claim 37 wherein said energy pulse system controller includes an operator input device to adjust the timing of said safe time period.

41. The heart-synchronized system of claim 40 wherein said operator input device adjusts the beginning of said safe time period with respect to said cyclical event.

42. The heart-synchronized system of claim 40 wherein said operator input device adjusts the end of said safe time period with respect to the beginning of said safe time period.

43. A heart-synchronized pulsed laser system for performing myocardial revascularization on a beating heart comprising:
a laser;
a sensor that senses a cyclical event related to the contraction and expansion of said beating heart; and
a laser controller responsive to said sensor that fires said laser to strike said beating heart only within a safe time period during a heart beat cycle, said time period being automatically determined by said controller with respect to said cyclical event.

44. A heart-synchronized method for performing myocardial revascularization on a beating heart of a patient comprising:
sensing a cyclical event related to the contraction and expansion of said beating heart with a sensor;
automatically determining a safe time period during a heart beat cycle to provide energy to strike said beating heart at a laser controller that is responsive to sensing of said cyclical event by said sensor,
producing laser pulses by a laser that is responsive to said laser controller to automatically fire said laser only within said safe time period,
directing laser pulses to strike desired locations at a wall of said beating heart, and
creating channels in said wall of said beating heart with said laser pulses.

45. A heart-synchronized method for performing myocardial revascularization on a beating heart of a patient comprising:
sensing a cyclical event related to the contraction and expansion of said beating heart with a sensor;
automatically determining a safe time period during a heart beat cycle to provide energy to strike said beating heart at an energy pulse system controller that is responsive to sensing of said cyclical event by said sensor,
producing energy pulses by an energy pulse system that is responsive to said energy pulse system controller to automatically provide energy only within said safe time period,
directing said energy pulses to strike desired locations at a wall of said beating heart, and
creating channels in said wall of said beating heart with said energy pulses.

46. The heart-synchronized method of claim 45 wherein said safe time period begins during the R wave.

47. The heart-synchronized method of claim 45 wherein said safe time period is a period in which firing of said energy pulse system will not cause fibrillation of the heart.

48. The heart-synchronized method of claim 45 wherein said safe time period is a period during which said heart is less sensitive electrically.

49. The heart-synchronized method of claim 45 wherein channels extend from an outside surface of said heart wall.

50. The heart-synchronized method of claim 45 wherein said directing of energy pulses directs them to desired locations on an outside surface of said heart.

51. The heart-synchronized method of claim 45 further comprising creating a small incision in said patient and wherein said directing includes directing through said small incision.

52. The heart-synchronized method of claim 45 wherein said sensing includes providing an electrical signal conveying information about said cyclical event, and said energy pulse system controller includes a threshold circuit that identifies said cyclical event when said electrical signal meets a threshold condition.

53. The heart-synchronized method of claim 45 further comprising, prior to said producing, generating an activation signal at an operator input device and providing said activation signal to said energy pulse system controller to activate firing of said energy pulse system.

54. The heart-synchronized method of claim 53 wherein said energy pulse system controller fires said energy pulse system during said safe time period subsequent to receiving said activation signal.

55. The heart-synchronized method of claim 45 wherein said channels extend all of the way through said wall of said heart.

56. The heart-synchronized method of claim 45 or 55 wherein said directing includes directing through ribs of said patient.

57. The heart-synchronized method of claim 45 wherein said energy pulses are electromagnetic energy.

58. The heart-synchronized method of claim 57 wherein said energy pulses are laser pulses.

59. The heart-synchronized method of claim 58 wherein said energy pulse system includes a $CO_2$ laser.

60. The heart-synchronized method of claim 58 wherein said directing includes directing a single continuous laser pulse within said safe time period of a heart beat cycle.

61. The heart-synchronized method of claim 58 wherein said laser pulses have constant laser energy during the time fired in said safe time period.

62. The heart-synchronized method of claim 45 wherein said sensing includes sensing an electrical signal that causes said heart to beat.

63. The heart-synchronized method of claim 62 wherein said electrical signal is an ECG signal of said beating heart, said ECG signal including Q, R, S, and T waves.

64. The heart-synchronized method of claim 63 wherein said safe time period begins at or after the R wave and extends past the S wave.

65. The heart-synchronized method of claim 64 wherein said safe time period ends before the T wave.

66. The heart-synchronized method of claim 45 further comprising adjusting the timing of said safe time period by said energy pulse system controller.

67. The heart-synchronized method of claim 66 wherein said adjusting includes adjusting the beginning of said safe time period by said energy pulse system controller with respect to said cyclical event.

68. The heart-synchronized method of claim 66 wherein said adjusting includes adjusting the end of said safe time period by said energy pulse system controller with respect to the beginning of said safe time period.

69. The heart-synchronized method of claim 68 wherein said energy pulse system controller includes an operator input device to adjust the timing of said safe time period.

70. The heart-synchronized method of claim 70 wherein said directing includes delivering system through a fiber-optic element.

71. The heart-synchronized method of claim 71 wherein said directing includes directing from terminal optics at a distal end of said fiber-optic element.

72. The heart-synchronized method of claim 71 wherein said automatically determining includes generating a beginning signal at a time related to the occurrence of said cyclical event by a trigger generator included in said energy pulse system controller, and using said beginning signal to automatically determine the beginning of said safe time period.

73. The heart-synchronized method of claim 72 wherein said energy pulse system controller includes a delay circuit connected to said trigger generator to provide said beginning signal at a predetermined delay time with respect to said cyclical event.

74. The heart-synchronized method of claim 72 wherein said trigger generator generates a trigger pulse to provide said beginning signal.

75. The heart-synchronized method of claim 72 wherein said energy pulse system controller includes a firing circuit that is responsive to said trigger generator to provide a firing signal to fire said energy pulse system in said safe time period.

76. The heart-synchronized method of claim 72 wherein said automatically determining also includes generating an end signal at said trigger generator, and using said end signal to automatically determine the end of said safe time period.

77. The heart-synchronized method of claim 76 wherein said energy pulse system controller includes time period duration circuit to provide said end signal at a predetermined delay time with respect to said beginning signal.

78. The heart-synchronized method of claim 76 wherein said trigger generator generates a trigger pulse to provide said end signal.

79. The heart-synchronized method of claim 76 wherein said trigger generator generates a trigger pulse with a leading edge and a trailing edge, said beginning signal being provided by said leading edge, said end signal being provided by said trailing edge.

80. A heart-synchronized pulsed laser system for performing transmyocardial revascularization on a beating heart comprising:
a laser;
means for sensing a contraction and expansion of a beating heart to be synchronized with the laser;
means, responsive to said means for sensing, for generating a trigger pulse having a width and a leading edge;
means for positioning the leading edge of said trigger pulse only at a time during the contraction and expansion cycle of the heartbeat which would not cause fibrillation of the heart;
means for defining the width of the trigger pulse to occur during the heartbeat cycle; and
means, responsive to said trigger pulse, for firing said laser to strike the beating heart at the time indicated by the trigger pulse position and for a period indicated by the width of the trigger pulse,
in which said means for sensing the contraction and expansion includes means for sensing an ECG signal of the beating heart, in which said means for positioning sets the leading edge of said trigger pulse in the period between R and T waves of the ECG signal, and in which said means for defining defines the pulse width of said trigger pulse in the period between the R and T waves of the ECG signal and extending past the S wave of the ECG signal.

81. The heart-synchronized pulsed laser system of claim 80, in which said laser includes a laser delivery system comprising a fiber-optic element.

82. The heart-synchronized pulsed laser system of claim 80, in which said laser includes a $CO_2$ laser.

83. The heart-synchronized pulsed laser system of claim 80, in which said laser includes a pulsed laser.

84. The heart-synchronized pulsed laser system of claim 83, in which said pulsed laser administers laser pulses to the heart during a period when the heart is least sensitive electrically.

85. The heart-synchronized pulsed laser system of any of claims 80–81, in which said means for positioning includes a threshold circuit for detecting a threshold value of the ECG signal.

86. The heart-synchronized pulsed laser system of claim 96, in which said means for positioning includes a delay circuit responsive to said threshold circuit for providing a delay between a position of the threshold value in the ECG signal and the leading edge of said trigger pulse.

87. The heart-synchronized pulsed laser method of claim 80, in which said defining includes defining the width of the trigger pulse in the period between the R and T waves of the ECG signal.

88. The heart-synchronized pulsed laser method of claim 87, in which said generating includes generating the trigger pulse in response to a threshold value of the ECG signal.

89. The heart-synchronized pulsed laser method of claim 88, in which said positioning includes providing a delay between a position of the threshold value in the ECG signal and the leading edge of said trigger pulse.

90. A heart-synchronized pulsed laser system for performing transmyocardial revascularization on a beating heart comprising:

a laser;

means for sensing a contraction and expansion of a beating heart to be synchronized with the laser;

means, responsive to said means for sensing, for generating a trigger pulse having a width and a leading edge;

means for positioning the leading edge of said trigger pulse only at a time during the contraction and expansion cycle of the heartbeat which would not cause fibrillation of the heart;

means for defining the width of the trigger pulse to occur during the heartbeat cycle; and means, responsive to said trigger pulse, for firing said laser to strike the beating heart at the time indicated by the trigger pulse position and for a period indicated by the width of the trigger pulse, in which said laser includes a laser beam delivery system, in which said laser delivery system includes a fiber-optic element, in which said laser delivery system includes a handpiece.

91. A heart-synchronized pulsed laser system for performing transmyocardial revascularization on a beating heart comprising:

a laser;

means for sensing a contraction and expansion of a beating heart to be synchronized with the laser;

means, responsive to said means for sensing, for generating a trigger pulse having a width and a leading edge;

means for positioning the leading edge of said trigger pulse only at a time during the contraction and expansion cycle of the heartbeat which would not cause fibrillation of the heart;

means for defining the width of the trigger pulse to occur during the heartbeat cycle; and means, responsive to said trigger pulse, for firing said laser to strike the beating heart at the time indicated by the trigger pulse position and for a period indicated by the width of the trigger pulse, in which said laser includes a laser beam delivery system, in which said laser delivery system includes a fiber-optic element, in which said laser delivery system includes terminal optics at a distal end of said fiber-optic element.

92. The heart-synchronized pulsed laser system of claim 91, in which said laser includes a pulsed laser capable of administering a pulsed laser beam to the heart during a period of the heartbeat cycle when the heart is least sensitive electrically.

93. A heart-synchronized pulsed laser system for performing transmyocardial revascularization on a beating heart comprising:

a laser;

means for sensing a contraction and expansion of a beating heart to be synchronized with the laser;

means, responsive to said means for sensing, for generating a trigger pulse having a width and a leading edge;

means for positioning the leading edge of said trigger pulse only at a time during the contraction and expansion cycle of the heartbeat which would not cause fibrillation of the heart;

means for defining the width of the trigger pulse to occur during the heartbeat cycle; and means, responsive to said trigger pulse, for firing said laser to strike the beating heart at the time indicated by the trigger pulse position and for a period indicated by the width of the trigger pulse, in which said laser includes a laser beam delivery system, in which said laser delivery system includes a fiber-optic element, in which said laser includes a pulsed laser capable of administering a pulsed laser beam to the heart during a period of the heartbeat cycle when the heart is least sensitive electrically.

94. A heart-synchronized pulsed laser system for performing transmyocardial revascularization on a beating heart comprising:

a laser;

means for sensing a contraction and expansion of a beating heart to be synchronized with the laser;

means, responsive to said means for sensing, for generating a trigger pulse having a width and a leading edge;

means for positioning the leading edge of said trigger pulse only at a time during the contraction and expansion cycle of the heartbeat which would not cause fibrillation of the heart;

means for defining the width of the trigger pulse to occur during the heartbeat cycle; and means, responsive to said trigger pulse, for firing said laser to strike the beating heart at the time indicated by the trigger pulse position and for a period indicated by the width of the trigger pulse, in which said laser includes a laser beam delivery system, in which said laser delivery system includes a fiber-optic element, in which said means for sensing the contraction and expansion includes means for sensing an ECG signal of the beating heart, in which said means for positioning includes a threshold circuit for detecting a threshold value of the ECG signal.

95. The heart-synchronized pulsed laser system of claim 94, in which said means for positioning includes a delay circuit responsive to said threshold circuit for providing a delay between a position of the threshold value in the ECG signal and the leading edge of said trigger pulse.

96. The heart-synchronized pulsed laser system of any one of claims 80–82, 90–94 or 95, in which:

said means for sensing the contraction and expansion includes an ECG unit for sensing an ECG signal of the beating heart;

said means for positioning includes a pulse positioning circuit that sets the leading edge of said trigger pulse in the period between the R and T waves of said ECG signal;

said means for defining includes a pulse width circuit that defines the pulse width of said trigger pulse in the period between said R and T waves of said ECG signal;

said means for generating a trigger pulse includes a trigger generator that generates a trigger pulse in response to said pulse positioning circuit and said pulse width circuit; and said means for firing includes a circuit inhibiting delivery of said trigger pulse to said laser and a switch enabling said inhibiting circuit to deliver said trigger pulse to said laser.

97. The heart-synchronized pulsed laser system of any of claims 94 or 95, in which said means for positioning sets the leading edge of said trigger pulse between the R wave and the T wave of the ECG signal.

98. The heart-synchronized pulsed laser system of claim 97, in which said means for positioning sets the leading edge of said trigger pulse during the R wave of the ECG signal.

99. A use of the heart-synchronized pulsed laser system for performing transmyocardial revascularization on a beating heart comprising:
   a laser;
   means for sensing a contraction and expansion of a beating heart to be synchronized with the laser;
   means, responsive to said means for sensing, for generating a trigger pulse having a width and a leading edge;
   means for positioning the leading edge of said trigger pulse only at a time during the contraction and expansion cycle of the heartbeat which would not cause fibrillation of the heart;
   means for defining the width of the trigger pulse to occur during the heartbeat cycle; and
   means, responsive to said trigger pulse, for firing said laser to strike the beating heart at the time indicated by the trigger pulse position and for a period indicated by the width of the trigger pulse,
said use comprising:
   employing said sensing means to sense a contraction and expansion of a beating heart to be synchronized with the laser;
   employing said means for generating to generate a trigger pulse having a width and a leading edge in response to said means for sensing;
   employing said means for defining to define the width of the trigger pulse to occur during the heartbeat cycle;
   employing said means for firing to fire said laser to strike the beating heart at a time indicated by the trigger pulse position and for a period indicated by the width of the trigger pulse.

100. A heart-synchronized pulse laser method for performing transmyocardial revascularization on a beating heart, comprising:
   generating a trigger pulse in response to an ECG signal of a beating heart to be synchronized with a laser, said trigger pulse having a width and a leading edge;
   positioning the leading edge of the trigger pulse only at a time during the ECG heartbeat cycle which would not cause fibrillation of the heart;
   defining the width of the trigger pulse to occur within the duration of the heartbeat cycle of the ECG signal; and
   applying the trigger pulse to fire the laser and to strike the beating heart at the time indicated by the trigger pulse position and for a period indicated by the width of the trigger pulse,
in which said positioning includes setting the leading edge of the trigger pulse in the period between R and T waves of the ECG signal.

101. A heart-synchronized pulse laser method for performing transmyocardial revascularization on a beating heart, comprising:
   generating a trigger pulse in response to an ECG signal of a beating heart to be synchronized with a laser, said trigger pulse having a width and a leading edge;
   positioning the leading edge of the trigger pulse only at a time during the ECG heartbeat cycle which would not cause fibrillation of the heart;
   defining the width of the trigger pulse to occur within the duration of the heartbeat cycle of the ECG signal; and
   applying the trigger pulse to fire the laser and to strike the beating heart at the time indicated by the trigger pulse position and for a period indicated by the width of the trigger pulse,
further comprising energizing the laser with a firing pulse in response to the trigger pulse, and delivering a laser beam comprised of laser pulses with the energized laser.

102. A heart-synchronized pulse laser method for performing transmyocardial revascularization on a beating heart, comprising:
   generating a trigger pulse in response to an ECG signal of a beating heart to be synchronized with a laser, said trigger pulse having a width and a leading edge;
   positioning the leading edge of the trigger pulse only at a time during the ECG heartbeat cycle which would not cause fibrillation of the heart;
   defining the width of the trigger pulse to occur within the duration of the heartbeat cycle of the ECG signal; and
   applying the trigger pulse to fire the laser and to strike the beating heart at the time indicated by the trigger pulse position and for a period indicated by the width of the trigger pulse,
further comprising applying laser pulses to strike the beating heart in the period between the R and T waves of the ECG signal.

103. A heart-synchronized pulse laser method for performing transmyocardial revascularization on a beating heart, comprising:
   generating a trigger pulse in response to an ECG signal of a beating heart to be synchronized with a laser, said trigger pulse having a width and a leading edge;
   positioning the leading edge of the trigger pulse only at a time during the ECG heartbeat cycle which would not cause fibrillation of the heart;
   defining the width of the trigger pulse to occur within the duration of the heartbeat cycle of the ECG signal; and
   applying the trigger pulse to fire the laser and to strike the beating heart at the time indicated by the trigger pulse position and for a period indicated by the width of the trigger pulse,
further comprising applying laser pulses to strike the beating heart through a laser delivery system that includes a fiber-optic element.

104. The heart-synchronized pulsed laser method of claim 103, in which said laser delivery system includes terminal optics at a distal end of said fiber-optic element.

105. A heart-synchronized pulse laser method for performing transmyocardial revascularization on a beating heart, comprising:
   generating a trigger pulse in response to an ECG signal of a beating heart to be synchronized with a laser, said trigger pulse having a width and a leading edge;
   positioning the leading edge of the trigger pulse only at a time during the ECG heartbeat cycle which would not cause fibrillation of the heart;
   defining the width of the trigger pulse to occur within the duration of the heartbeat cycle of the ECG signal; and
   applying the trigger pulse to fire the laser and to strike the beating heart at the time indicated by the trigger pulse position and for a period indicated by the width of the trigger pulse,
further comprising energizing the laser in the period between the R and T waves of the ECG signal, the energized laser providing a laser beam comprised of laser pulses, delivering said laser beam through a laser delivery system that includes a fiber-optic element, and striking the beating heart with the laser beam.

106. The heart-synchronized pulsed laser method of any one of claims 87–105 in which said defining includes defining the width of the trigger pulse to end after the S wave and before the T wave of the ECG signal.

107. A heart-synchronized pulsed laser method for performing transmyocardial revascularization on a beating heart of a patient, comprising:

provoding a pulsed laser system including a laser and a laser beam delivery system, the laser delivery system comprising a fiber-optic element;

generating a trigger pulse in response to an ECG signal of the beating heart to be synchronized with said laser, said trigger pulse having a width and a leading edge;

positioning the leading edge of the trigger pulse at a time during the ECG heartbeat cycle which would not cause fibrillation of the heart;

defining the width of the trigger pulse to occur within the duration of the heartbeat cycle of the ECG signal;

applying the trigger pulse to fire the laser to produce a laser beam; and delivering the laser beam through the fiber-optic element to strike the beating heart at the time indicated by the trigger pulse position and for a period indicated by the width of the trigger pulse.

108. The heart-synchronized pulsed laser method of claim 107, in which delivering the laser beam further includes delivering the laser beam through a simple incision in the patient that provides access to the beating heart.

109. The heart-synchronized pulsed laser method of claim 107, in which the laser delivery system further includes terminal optics at a distal end of the fiber optic element.

110. The heart-synchronized pulsed laser method of claim 107, in which the laser beam is comprised of a pulsed laser beam.

111. The heart-synchronized pulsed laser method of claim 110, in which delivering the laser beam further includes delivering the laser beam through a simple incision in the patient that provides access to the beating heart, in which said positioning includes setting the leading edge of the trigger pulse in the period between R and T waves of the ECG signal, and in which said defining includes defining the width of the trigger pulse in the period between the R and T waves of the ECG signal.

* * * * *